US006939675B2

(12) United States Patent
Gocke et al.

(10) Patent No.: US 6,939,675 B2
(45) Date of Patent: Sep. 6, 2005

(54) DETECTION OF EXTRACELLULAR TUMOR-ASSOCIATED NUCLEIC ACID IN BLOOD PLASMA OR SERUM USING NUCLEIC ACID AMPLIFICATION ASSAYS

(75) Inventors: Christopher D. Gocke, Ellicott City, MD (US); Michael S. Kopreski, Long Valley, NJ (US); Floyd A. Benko, Palmyra, PA (US)

(73) Assignee: The Penn State Research Foundation, University Park, PA (US)

( * ) Notice: Subject to any disclaimer, the term of this patent is extended or adjusted under 35 U.S.C. 154(b) by 127 days.

(21) Appl. No.: 10/298,816

(22) Filed: Nov. 18, 2002

(65) Prior Publication Data

US 2003/0143600 A1 Jul. 31, 2003

Related U.S. Application Data

(63) Continuation of application No. 09/642,952, filed on Aug. 21, 2000, now Pat. No. 6,521,409, which is a continuation of application No. 08/818,058, filed on Mar. 14, 1997, now Pat. No. 6,156,504.
(60) Provisional application No. 60/028,180, filed on Oct. 15, 1996, provisional application No. 60/026,252, filed on Sep. 17, 1996, and provisional application No. 60/013,497, filed on Mar. 15, 1996.

(51) Int. Cl.[7] ............................ C12Q 1/68; C12P 19/34

(52) U.S. Cl. ......................................... 435/6; 435/91.2

(58) Field of Search ........................... 435/6, 7.1, 91.1, 435/91.2; 536/22.1, 23.1, 24.3, 33

(56) References Cited

U.S. PATENT DOCUMENTS

| 4,965,188 A | 10/1990 | Mullis |
| 5,182,377 A | 1/1993 | Manos |
| 5,283,898 A | 2/1994 | Manos |
| 5,496,699 A | 3/1996 | Sorenson |
| 5,512,439 A | 4/1996 | Hornes |
| 5,512,441 A | 4/1996 | Ronai |
| 5,527,676 A | 6/1996 | Vogelstein |
| 5,527,898 A | 6/1996 | Bauer |
| 5,639,871 A | 6/1997 | Bauer |
| 5,705,627 A | 1/1998 | Manos |
| 5,814,448 A | 9/1998 | Silverstein |
| RE36,713 E | 5/2000 | Vogelstein et al. |
| 6,090,566 A | 7/2000 | Vogelstein |
| 6,383,733 B1 * | 5/2002 | Beug et al. ..................... 435/4 |

FOREIGN PATENT DOCUMENTS

| WO | WO 8900206 | 11/1989 |
| WO | WO 9615139 | 5/1996 |
| WO | WO 9516792 | 6/1996 |
| WO | WO 9734015 | 9/1997 |

OTHER PUBLICATIONS

LeJeune et al Amphiregulin, Epidermal Growth Factor Receptor and Estrogen Receptor Expression in Human Primary Breast Cancer, Aug. 1, 1993, Cancer Research, vol. 53, pp. 3597–3602.*
Aggarwal, et al., (Mar. 1975) "Cell–Surface–Associated Nucleic Acid in Tumorigenic Cells Made Visible with Platinum–Pyrimidine Complexes by Electron Microscopy." *Proc. Nat. Acad. Sci.*, vol. 72, No. 3, pp. 928–932.
Aoki et al., (Sep. 1995) "Liposome–mediated in vivo Gene Transfer of Antisense K–ras Construct Inhibits Pancreatic Tumor Dissemination in the Murine Peritoneal Cavity." *Cancer Research*, 55:3810–3816.
Ausuker et al., Editions Short Protocols in Molecular Biology John Wiley & Sons, New. York pp. 72–80, 1989.
Barz et al., (1985) "Characterization of cellular and extracellular plasma membrane vesicles from a non–metastasizing lymphoma (Eb) and its metastasizing variant (EESb)." *Biochimica et Biophysica Acta*, 814:7–84.
Blackburn et al., (1991) "Electrochemiluminescence Detection of Immunoassays and DNA Probe Assays for Clinical Diagnostics." *Clin. Chem.*, vol. 37, No. 9, pp. 1534–1539.

(Continued)

*Primary Examiner*—Kenneth R. Horlick
(74) *Attorney, Agent, or Firm*—McDonell Boehnen Hulbert & Berghoff

(57) ABSTRACT

This invention relates to detection of specific extracellular nucleic acid in plasma or serum fractions of human or animal blood associated with neoplastic or proliferative disease. Specifically, the invention relates to detection of nucleic acid derived from mutant oncogenes or other tumor-associated DNA, and to those methods of detecting and monitoring extracellular mutant oncogenes or tumor-associated DNA found in the plasma or serum fraction of blood by using rapid DNA extraction followed by nucleic acid amplification with or without enrichment for mutant DNA. In particular, the invention relates to the detection, identification, or monitoring of the existence, progression or clinical status of benign, premalignant, or malignant neoplasms in humans or other animals that contain a mutation that is associated with the neoplasm through detection of the mutated nucleic acid of the neoplasm in plasma or serum fractions. The invention permits the detection of extracellular, tumor-associated nucleic acid in the serum or plasma of humans or other animals recognized as having a neoplastic or proliferative disease or in individuals without any prior history or diagnosis of neoplastic or proliferative disease. The invention provides the ability to detect extracellular nucleic acid derived from genetic sequences known to be associated with neoplasia, such as oncogenes, as well as genetic sequences previously unrecognized as being associated with neoplastic or proliferative disease. The invention thereby provides methods for early identification of colorectal, pancreatic, lung, breast, bladder, ovarian, lymphoma and all other malignancies carrying tumor-related mutations of DNA and methods for monitoring cancer and other neoplastic disorders in humans and other animals.

13 Claims, 6 Drawing Sheets

OTHER PUBLICATIONS

Bobo et al., (Sep. 1990) "Diagnosis of Chylamydia trachomatis Cervical Infection by Detection of Amplified DNA with and Enzyme Immunoassay." *Journal of Clinical Microbiology*, vol. 28, No. 9, 1968–973.

Boland, Richard, (Sep. 1996) "Setting microsatellites free" *Nature Medicine*, vol. 2, No. 9, pp. 972–974.

Boom et al., (Mar. 1990) "Rapid and Simple Method for Purification of Nucleic Acids." *Journal of Clinical Microbiology*, vol. 28, No. 3, pp. 495–303.

Boom et al., (Sep. 1991) " Rapid Purification of Hepatitis B Virus DNA from Serum." *Journal of Clinical Microbiology*, vol. 29, No. 9, pp. 1804–1811.

Bos et al., (May 1987) "Prevalence of ras gene mutations in human colorectal cancers." *Nature*, vol. 327, pp. 293–297.

Carr et al., (Nov. 1985) "Circulating Membrane Vesicles In Leukemic Blood." *Cancer Research*, 45: 5944–5951.

Chaubert et al., (1994) "K–ras Mutations and p53 Alterations in Neoplastic and Nonneoplastic Lesions Associated with Longstanding Ulcerative Colitis." *Amer. Jrnl. Of Path.*, vol. 144, No. 4, pp. 767–774.

Chen et al., (1991) "A Method to Detect ras Point Mutations in Small Subpopulations of Cells." *Analytical Biochemistry*, 195: 51–56.

Chen et al., (Sep. 1996) "Microsatellite alterations in plasma DNA of small cell lung cancer patients." *Nature Medicine*, vol. 2, No. 9, pp. 1033–1035.

Chen et al., "Detecting Tumor–related Alteractions in Plasma or Serum DNA of patients Diagnosed with Breast Cancer," Clinical Cancer Research, Sep. 1999 vol. 5, 2297–2302.

Cheung et al., (Oct. 1994) "Rapid and Sensitive Method for Detection of Hepatitis C Virus RNA by Using Silica Particles." vol. 32, No. 10, pp. 2593–2597.

Chomczynski, Piotr, (1993) "A Reagent For the Single–Step Simultaneous Isolation of RNA, DNA and Proteins from Cell and Tissue Samples." *Biotechniques*, vol. 15, No. 3, pp. 532–536.

Christa et al ., (1992) "Nested polymerase chain reaction of cellular DNA in plasma: a rapid method to investigate th collagen type I A2 MspI polymorphic restriction site in alcoholic patients." *Human Genetics*, 88: 537–540.

Chua et al., 1996, Int. J. Cancer, 69: 54–59.

Cleary et al., "Cloning and Structural Analysis of cDNAs for bcl–2 and a Hybrid bcl–2/Immunoglobulin Transcript Resulting from the t(14;18) Translocation ," Cell. 47:19–28, Oct. 10, 1985.

Coutlee et al., (1989) "Immunodetection of DNA with Biotinylated RNA Probes: A Study of Reactivity of a Monoclonal Antibody to DNA–RNA Hybrids." *Analytical Biochemistry*, 181: 96–105.

DiCesare et al., (1993) "A High–Sensitivity Electrochemiluminescence–Based Detection System for Automated PCR Product Quantitation." *BioTechniques*, vol. 15, No. 1, pp. 152–157.

Emanuel et al., (1993) "Amplification of Specific Gene Products from Human Serum." *GATA*, vol. 10, No. 6, pp. 144–146.

Fearon et al., (Jun. 1990) "A Genetic Model for Colorectal Tumorigenesis." *Cell*, vol. 61, pp. 759–767.

Fearon et al., (Oct. 1987) "Clonal Analysis of Human Colorectal Tumors." *Science*, vol. 238, pp. 193–196.

Fedorov et al., (1987) DNA Assay In Human Blood Plasma. Translated from *Byuleten Eksperiments! Biologii i Meditsiny*, vol. 102, No. 9, pp. 281–281.

Fey et al., (1991) "The Polymerase Chain Reaction: A New Tool for the Detection of minimal Residual Disease In Haematological Malignancies." *Eur. J. Cancer.*, vol. 27, No. 1, pp. 89–94.

Finney et al., (Jun. 1993) "Predisposition of Neoplastic Transformation Caused by Gene Replacement of H–ras1." *Science*, vol. 260, pp. 1524–1527.

Fournie et al., (1986) "Recovery of Nanogram Quantities of DNA from Plasma and Quantitative Measurement Using Labeling by Nick Translation." *Analytical Biochemistry*, 158: 220/256.

Fournie et al., (Feb. 1995) "Plasma DNA as a marker of cancerous cell death. Investigation in patients suffering from lung cancer and in nude mice bearing human tumours." *Cancer Letters*, 91: 221–227.

Fowke et al., (1995) "Genetic analysis of human DNA recovered from minute amounts of serum of plasma." *Journal of Immunological Methods*, 180, pp. 45–51.

Gocke et al., "p53 and APC Mutations are Detectable in the Plasma and Serum of Patients with Colorectal Cancer (CRC) or Adenomas," Annals New York Academy of Science, p 44–50.

Gocke et al., "Serum BCL2/IGH DNA in Follicular Lymphoma Patients: A Minimal Residual Disease Marker," Leukemia and Lymphoma 2000, 39 (1–2) pp. 165–172.

Greenblatt et al., (1994) "Mutations in the p53 Tumor Suppressor Gene: Clues to Cancer Etiology and Molecular Pathogenesis." *Cancer Research*, 54:4855–4878.

Hamiliton, Stanley., (Sep. 1992) "Molecular Genetics of Colorectal Carcinoma." *Cancer Supplement*, vol. 70, No. 5, pp. 1216–1221.

Hollstein et al., (1994) "Database of p53 gene somatic mutations in human tumors and cell lines." *Nucleic Acids Research*, vol. 22, No. 17, pp. 3551–3555.

Juckett et al., (Sep. 1982) "Actions of cis–Diamminedichloroplatinum on Cell Surface Nucleic Acids in Cancer Cells as Determined by Cell Electrophoresis Techniques." *Cancer Research*, 42: 3565–3573.

Kahn et al., (1991) "Rapid and sensitive nonradioactive detection of mutant K–ras genes via 'enriched' PCR amplification." *Oncogene*, 6: 1079–1083.

Kamm et al., (1972) "Nucleic Acid Concentrations in Normal Human Plasma." *Clinical Chemistry*, vol. 18, No. 6, pp. 519–522.

Karet et al., (1994) "Quantification of mRNA in Human Tissue Using Fluorescent Nested Reverse–Transcriptase Polymerase Chain Reaction." *Analytical Biochemistry*, 220: 384–390.

Kievits et al., (1991) "NASBA isothermal enzymatic in vitro nucleic acid amplification optimized for the diagnosis of HIV–1 infection." *Journal of Virological Methods*, 35: 273–286.

Kimura et al., 1991, J. Infect Dis. 164:289–293.

Kopreski et al., Somatic Mutation Screening: Identification of Individuals Harboring K–ras Mutations with the Use of Plasma DNA, Journal of the National Cancer Institute, vol. 92, No. 11, Jun. 7, 2000.

Kondo et al., (Mar. 1994) "Detection of Point Mutations in the K–ras Oncogene at Codon 12 in Pure Pancreatic Juice for Diagnosis of Pancreatic Carcinoma." *Cancer*, vol. 23, No. 6, pp. 1589–1594.

Landergren Trends or Genetics 9:199–204, Jun. 1993.

Landgraf et al., (1991) "Direcct Analysis of Polymerase Chain Reaction Products Using Enzyme–linked Immunosorbent Assay Techniques." *Analytical Biochemsitry*, 198:86–91.

Landgraf et al., (1991) "Quantitative Analysis of Polymerase Chain Reaction (PCR) Products Using Primers Labeled with Biotin and a Fluorescent Dye." *Analytical Biochemistry*, 193: 231–235.

Leffort et al., "Point mutations of the K–Ras gene present in the DNA of colorectal tumors are found in the blood plasma DNA of the patients," Proceedings of the American Association for Cancer Research Annual 36:557, 1995.

Leon et al., (1981) "A Comparison of DNA and DNA–Binding Protein Levels in Malignant Disease." *Europ. J. Cancer*, vol. 17, No. 5, pp. 533–538.

Leon et al., (Mar. 1977) "Free DNA in the Serum of Cancer Patients and the Effect of Therapy." *Cancer Research*, 37: 646–650.

Lowy et al., (Nov. 1991) "Regulation of p21ras Activity." *Trends of Genetics*, 7: 346–351.

Martin et al., (1992) "A Method for Using Serum of Plasma as a Source of DNA or HLA Typing." *Human Immunology*, 33: 108–113.

Mayall et al., J. Clin. Pathol. 1998, 51:611–613.

Mulcahy et al., (Sep. 1996) "Cancer and mutant DNA in blood plasma." *Science*,vol. 348, pp. 628.

Mulcany et al., " A Prospective Study of K–ras Mutations in the Plasma of Pancreatic Cancer Patients," Clinical Cancer Research, 4:271–5 (Feb. 1998).

Nawroz et al., (Sep. 1996) "Microsatellite alterations in serum DNA of head and neck cancer patients." *Nature Medicine*, vol. 2, No. 9, pp. 1035–1037.

Nelson et al., (Feb. 1996) "Detection of K–ras gene mutations in non–neoplastic lung tissue and lung cancers,"*Cancer Letters* 103 (1996) 115–121.

Olsen et a., 1996, Int. J. Cancer 68:415–419.

Oudejans et al., (1991) "Differential Activation of RAS Genes By Point Mutation In Human Colon Cancer With Metastases to Either Lung of Liver." *Int. J. Cancer*, 49: 875–879.

Pellegata et al., (1992) "Detection of K–ras Mutations by Denaturing Gradient Gel Electrophoresis (DGGE): A Study of Pancreatic Cancer." *Anticancer Research*, 12:1731–1736.

Procrand et al. Mutation Research 288:113–121, Jul. 1993.

Rex et al., Gastroenterology 1997; 11:24–28.

Rhodes et al., (1995) "PCR–Detection of Tumor–Derived p53 DNA in Cerebrospinal Fluid."*Am. J. Clin. Path.*, 103:404–408.

Shapiro et al., (Jun. 1983) "Determination of Circulating DNA Levels in Patients with Benign or Malignant Gastrointestinal Disease." *Cancer*, vol. 51, No. 11, pp. 2116–2120.

Shirasawa et al., (Apr. 1993) "Altered Growth of Human Colon Cancer Cell Lines Disrupted at Activated Ki–ras." *Science*, vol. 260, pp. 85–88.

Sidransky, et al., (1992) "Identification of ras Oncogene Mutations in the Stool of Patients with Curable Colorectal Tumors." *Science*, vol. 256, pp. 102–105.

Sidransky et al., "What we know and what we need to learn," Annals new York Academy of Sciences, pp1–4.

Sorenson et al., (Jan. 1994) "Soluble Normal and Mutated DNA Sequence from Single–Copy Genes in Human Blood." *Cancer Epidemiology, Biomarkers & Prevention*, vol. 3, pp. 67–71.

Sorenson et al., Detection of Mutated KRAS2 Sequences as Tumor Markers in Plasma/Serum of Patients with Gastrointestinal Cancer, Clinical Cancer Research, 6:2129–37 (Jun. 2000).

Stork et al., (1991) "Detection of K–ras mutations in pancreatic and hepatic neoplasms by non–isotopic mismatched polymerase chain reaction." *Oncogene*, 6: 857–862.

Stroun et al., (1986) "Isolation and Characterization of DNA from the Plasma of Cancer Patients." *European Journal of Cancer*, vol. 23, No. 6, pp. 707–712.

Stroun et al., (1989) "Neoplastic Characteristics of the DNA Found in the Plasma of Cancer Patients." *Oncology*, 46: 318–322.

Tada et al., (Jun. 1993) "Detection of ras Gene Mutations in Pancreatic Juice and Peripheral Blood of Patients with Pancreatic Adenocarcinoma." *Cancer Research*, 53:2472–2474.

Taylor et al., (Date Uknown) "Shedding of Plasma Membrane Fragements. Neoplastic and Developmental Importance." *Membrane Fragment Shedding*, Chapter 3, pp. 33–57.

Tseng et al., 1999, J. Clin. Oncol. 17:1391–1396.

Urdea et al., (1991) "Branched DNA amplification multimers for the sensitive, direct detection of human hepatitis viruses."*Nucleic Acids Research*, Symposium Series No. 24, pp. 197–200.

Urdea et al., (1993) Direct and quantitiative detection of HIV–1 RNA in human plasma with a branched DNA signal amplification assay. *Aids*, 7 (suppl. 2): S11–S14.

Vandamme et al., (1995) "Detection of HIV–1 RNA in plasma and serum samples using the NASBA amplification system compared to RNA–PCR." *Journal of Virological Methods*, 52:121–132.

Van Mansfeld et al., "PCR–based Approaches for Detection of Mutated ras Genes," PCR Methods and Applications, pp. 211–216.

Vasioukhin et al., (1994) "Point mutations of the N–ras gene in the blood plasma DNA of patients with myelodysplastic syndrome of acute myelogenous leukaemia." *British Journal of Haematology*, 86: 774–779.

Vasyukhin et al., (Date Unknown) "K–Ras Point Mutations in the Blood Plasma DNA of Patients with Colorectal Tumors."

Vogelstein et al., (Sep. 1988) "Genetic Alterations During Colorectal–Tumor Development." *The New England Journal of Medicine*, vol. 319, No. 9, pp. 525–532.

Wang et al., (Dec. 1989) "Quantitation of mRNA by the polymerase chain reaction." *Proc. Natl. Acad. Sci.*, vol. 86, pp. 9717–9721.

Winawer et al., The New–Eng. Journal of Medicine vol. 328, No. 13:901–906.

Yamagata et al., (Feb. 1994) "Lower Incidence of K–ras Codon 12 Mutation in Flat Colorectral Adenomas than in Polypoid Adenomas." *Jpn. J. Cancer Res.*, 85: 147–151.

* cited by examiner

DETECTION OF EXTRACELLULAR TUMOR-ASSOCIATED NUCLEIC ACID IN BLOOD PLASMA OR SERUM USING NUCLEIC ACID AMPLIFICATION ASSAYS

This application is a continuation U.S. Ser. No. 09/642,952, filed Aug. 21, 2000 now U.S. Pat. No. 6,521,409, which is a continuation of U.S. Ser. No. 08/818,058, filed Mar. 14, 1997, now U.S. Pat. No. 6,156,054, which is a continuation-in-part of U.S. Provisional Application, Ser. No. 60/028,180, filed Oct. 15, 1996, and U.S. Provisional Application, Ser. No. 60/026,252, filed Sep. 17, 1996, and U.S. Provisional Application, Ser. No. 60/013,497, filed Mar. 15, 1996, each of which provisional applications is now abandoned, the entire disclosure of each of which is hereby incorporated by reference.

BACKGROUND OF THE INVENTION

1. Field of the Invention

This invention relates to methods for detecting specific extracellular nucleic acid in plasma or serum fractions of human or animal blood associated with neoplastic or proliferative disease. Specifically, the invention relates to detection of nucleic acid derived from mutant oncogenes or other tumor-associated DNA, and to methods of detecting and monitoring extracellular mutant oncogenes or tumor-associated DNA found in the plasma or serum fraction of blood by using rapid DNA extraction and nucleic acid amplification. In particular, the invention relates to the detection, identification, or monitoring of the existence, progression or clinical status of benign, premalignant, or malignant neoplasms in humans or other animals that contain a mutation that is associated with the neoplasm, through detection of the mutated nucleic acid of the neoplasm in plasma or serum fractions. The invention permits the detection of extracellular, tumor-associated nucleic acid in the serum or plasma of humans or other animals recognized as having a neoplastic or proliferative disease or in individuals without any prior history or diagnosis of neoplastic or proliferative disease. The invention provides the ability to detect extracellular nucleic acid derived from genetic sequences known to be associated with neoplasia, such as oncogenes, as well as genetic sequences previously unrecognized as being associated with neoplastic or proliferative disease. The invention thereby provides methods for early identification of colorectal, pancreatic, lung, breast, bladder, ovarian, lymphoma and all other malignancies carrying tumor-related mutations of DNA, and methods for monitoring cancer and other neoplastic disorders in humans and other animals.

2. Description of the Related Art

Neoplastic disease, including most particularly that collection of diseases known as cancer are a significant part of morbidity and mortality in adults in the developed world, being surpassed only by cardiovascular disease as the primary cause of adult death. Although improvements in cancer treatment have increased survival times from diagnosis to death, success rates of cancer treatment are more closely related to early detection of neoplastic disease that enable aggressive treatment regimes to be instituted before either primary tumor expansion or metastatic growth can ensue.

Oncogenes are normal components of every human and animal cell, responsible for the production of a great number and variety of proteins that control cell proliferation, growth regulation, and cell death. Although well over one hundred oncogenes have been described to date—nearly all identified at the deoxyribonucleic acid (DNA) sequence level—it is likely that a large number of oncogenes remains to be discovered.

Genetic mutation as the result of inborn genetic errors or environmental insult have long been recognized as playing a causative role in the development of neoplastic disease. Within the last twenty years, however, the sites of such mutations have been recognized to be within oncogenes, and mutation of such oncogenes has been found to be an intrinsic and crucial component of premalignant and malignant growth in both animals and humans. When an oncogene is mutated it alters the growth or regulation of the cell through changes in the protein it encodes. If the mutation occurs in a certain region or regions of the gene, or involves a regulatory region of a gene, a growth advantage may accrue to a cell having a mutated oncogene. Many malignant tumors or cell lines derived from them have been shown to contain one or more mutated oncogenes, and it is possible that every tumor contains at least one mutant oncogene.

Mutated oncogenes are therefore markers of malignant or premalignant conditions. It is also known that other, non-oncogenic portions of the genome may be altered in the neoplastic state. Nucleic acid based assays can detect both oncogenic and non-oncogenic DNA, whether mutated or non-mutated. In particular, nucleic acid amplification methods (for example, the polymerase chain reaction) allow the detection of small numbers of mutant molecules among a background of normal ones. While alternate means of detecting small numbers of tumor cells (such as flow cytometry) have generally been limited to hematological malignancies (Dressler and Bartow, 1989, *Semin. Diag. Pathol.* 6: 55–82), nucleic acid amplification assays have proven both sensitive and specific in identifying malignant cells and for predicting prognosis following chemotherapy (Fey et al., 1991, *Eur. J. Cancer* 27: 89–94).

Various nucleic acid amplification strategies for detecting small numbers of mutant molecules in solid tumor tissue have been developed, particularly for the ras oncogene (Chen and Viola, 1991, *Anal. Biochem.* 195: 51–56; Kahn et al., 1991, *Oncogene* 6: 1079–1083; Pellegata et al., 1992, *Anticancer Res.* 12: 1731–1736; Stork et al., 1991, *Oncogene* 6: 857–862). For example, one sensitive and specific method identifies mutant ras oncogene DNA on the basis of failure to cleave a restriction site at the crucial 12th codon (Kahn et al., 1991, ibid.). Similar protocols can be applied to detect any mutated region of DNA in a neoplasm, allowing detection of other oncogene DNA or tumor-associated DNA. Since mutated DNA can be detected not only in the primary cancer but in both precursor lesions and metastatic sites (Dix et al., 1995, *Diagn. Molec. Pathol.* 4: 261–265; Oudejans et al., 1991, *Int. J. Cancer* 49: 875–879), nucleic acid amplification assays provide a means of detecting and monitoring cancer both early and late in the course of disease.

While direct analysis of tumor tissue is frequently difficult or impossible (such as in instances of occult, unrecognized disease), peripheral blood is easily accessible and amenable to nucleic acid amplification assays such as those mentioned above. Many studies use nucleic acid amplification assays to analyze the peripheral blood of patients with cancer in order to detect intracellular DNA extracted from circulating cancer cells, including one study which detected the intracellular ras oncogene from circulating pancreatic cancer cells (Tada et al., 1993, *Cancer Res.* 53: 2472–4). However, it must be emphasized that almost universally these studies attempt to use nucleic acid-based amplification assays to detect extracted intracellular DNA within circulating cancer cells.

The assay is performed on the cellular fraction of the blood, i.e. the cell pellet or cells within whole blood, and the serum or plasma fraction is ignored or discarded prior to analysis. Since such an approach requires the presence of metastatic circulating cancer cells (for non-hematologic tumors), it is of limited clinical use in patients with early cancers, and it is not useful in the detection of non-invasive neoplasms or pre-malignant states.

It has not been generally recognized that nucleic acid amplification assays can detect tumor-associated extracellular mutated DNA, including oncogene DNA, in the plasma or serum fraction of blood. Furthermore, it has not been recognized that this can be accomplished in a clinically useful manner, i.e. rapidly within one day, or within less than 8 hours. It is known that small but significant amounts of normal DNA circulate in the blood of healthy people (Fedorov et al., 1986, *Bull. Exp. Biol. Med.* 102: 1190–2; Leon et al., 1977, *Cancer Res.* 37: 646–50), and this amount has been found to increase in cancer states (Shapiro et al., 1983, *Cancer* 51: 2116–20; Stroun et al., 1989, *Oncology* 46: 318–322). However, these studies did not employ nucleic acid amplification methods, nor did they demonstrate the presence of mutant DNA or specific oncogene DNA in peripheral blood. Thus, the DNAs detected in blood in these reports were not definitively ascribed to cancer; nor could clinical utility be realized. In addition, it had been generally presumed by those with skill in the art that circulating extracellular DNA either does not exist or would be of no clinical utility since it would be expected to be rapidly digested by plasma DNases. However, inhibitors of DNase appear to be present in the plasma of cancer patients (Leon et al., 1981, *Eur. J. Cancer* 17: 533–8). Furthermore, extracellular DNA may exist in proteo-lipid complexes resistant to DNase (Stroun et al., 1987, *Eur. J. Cancer Clin. Oncol.* 23: 707–12). In addition, DNA from tumor cells may be present in the extracellular fluid because of secretion or shedding from viable tumor in the form of proteo-lipid complexes, release of apoptotic bodies from apoptotic tumor cells, or release of free or protein-bound DNA from necrotic or lysed cancer cells. For example, shedding of phospholipid vesicles from tumor cells is well described (Barz et al., 1985, *Biochim. Biophys. Acta* 814: 77–84; Taylor & Blak, 1985, "Shedding of plasma membrane fragments. Neoplastic and developmental importance," in: Steinberg (ed) *The Cell Surface in Development and Cancer, Developmental Biology*, Plenum Press, New York, pp. 33–57), and similar vesicles have been shown to circulate in the blood of patients with cancer (Carr et al., 1985, *Cancer Res.* 45: 5944–51). Furthermore, DNA has been shown to be present on the cell surface of tumor cells (Aggarwal et al., 1975, *Proc. Natl. Acad. Sci. USA* 72: 928–32; Juckett & Rosenberg, 1982, *Cancer Res.* 42: 3565–73).

Detection of a mutant oncogene in peripheral blood plasma or serum has been the subject of reports in the prior art (see, for example, Sorenson et al., 1994, *Cancer Epidemiology, Biomarkers & Prevention* 3: 67–71; Vasioukhin et al., 1994, *Br. J. Haematol.* 86: 774–9; Vasyukhin et al., 1994, "K-ras point mutations in the blood plasma DNA of patients with colorectal tumors," in Verna & Shamoo (eds), *Biotechnology Today*, Ares-Serono Symposia Publications, pp. 141–150). Mutant ras oncogenes have been demonstrated in plasma or serum using polymerase chain reaction. However, the methods employed by these groups required time-consuming and technically demanding approaches to DNA extraction and are thus of limited clinical utility. Thus, methods that permit medically useful, rapid, and timely extraction and sensitive detection of extracellular tumor-associated or extracellular mutated oncogenic DNA are not known in the art.

SUMMARY OF THE INVENTION

This invention provides methods for detecting the presence of extracellular DNA in blood plasma or serum fractions, said DNA being associated with a neoplastic or proliferative disease state in an animal or a human. The invention provides methods for extracting, amplifying and detecting extracellular DNA associated with a neoplastic or proliferative disease state in an animal or a human and that are used for the detection, monitoring, or evaluation of cancer or premalignant conditions.

In a first aspect, the invention provides a method for detecting extracellular tumor-derived or tumor-associated nucleic acid in a plasma or serum fraction of a blood sample, for diagnosis, detection, monitoring, evaluation or treatment of a neoplastic or proliferative disease in an animal or a human. The method provided by the invention comprises the steps of: first, purifying extracellular nucleic acid from plasma or serum to prepare a homogeneous preparation of extracted nucleic acid; second, specifically amplifying a portion of the extracted nucleic acid to provide an amplified nucleic acid fraction comprising a nucleic acid that is associated with neoplastic or proliferative disease; and third, detecting the amplified nucleic acid fragment that is associated with neoplastic or proliferative disease in the amplified nucleic acid fraction. In preferred embodiments of this aspect of the invention, extracted nucleic acid is amplified using an amplification method selected from the group consisting of polymerase chain reaction, ligase chain reaction, branched DNA signal amplification, boomerang DNA amplification, Q-beta replication, transcription-based amplification, isothermal nucleic acid sequence based amplification, self-sustained sequence replication assay, strand displacement activation, cycling probe technology, and combinations or variations thereof. In another preferred embodiment, the nucleic acid is derived from a nucleic acid encoding an oncogene or other tumor-associated DNA.

The invention also provides a method for detecting extracellular tumor-derived or tumor-associated nucleic acid in a plasma or serum fraction of a blood sample, for diagnosis, detection, monitoring, evaluation or treatment of a neoplastic or proliferative disease in an animal or a human comprising the additional step of digesting the extracted nucleic acid fraction with an enzyme that specifically cleaves nucleic acid in the fraction that is associated with a neoplastic or proliferative disorder, whereby enzymatic cleavage thereof is accomplished in nucleic acid derived from a wildtype allele of said nucleic acid that is not associated with a neoplastic or proliferative disease, but wherein enzymatic cleavage is not accomplished in nucleic acid derived from a mutant or variant allele that is associated with a neoplastic or proliferative disease. Preferably, digestion of the extracted extracellular nucleic acid with an enzyme, preferably an endonuclease, most preferably a restriction enzyme, specifically cleaves wildtype but not mutant DNA in the portion of the sequence between the positions of the oligonucleotide primers used to amplify the DNA. Thus, wildtype DNA in the sample cannot be amplified after restriction enzyme digestion, whereas mutant DNA can be amplified, and is preferentially amplified using the methods of the invention. In a preferred embodiment, the amplification reaction is performed in the presence of a thermoresistant or thermostable restriction endonuclease, which endonuclease specifically cleaves wildtype forms of extracellular tumor-derived or tumor-associated nucleic acid species and thereby inhibits amplification of said species in the amplification reaction. In another preferred embodiment, the amplification step of the methods of the invention are performed using oligonucleotide primers that produce a restriction endonuclease recognition site in nucleic acid in the fraction that is associated with a neoplastic or proliferative disease within the nucleotide sequence of said nucleic acid fragment, whereby enzymatic cleavage thereof is accomplished in a nucleic acid fragment derived from a wildtype allele of said nucleic acid that is not associated with a neoplastic or proliferative disease, and wherein enzymatic cleavage is not accomplished in a nucleic acid fragment derived from a mutant or variant allele that is associated with a neoplastic or proliferative disease, and wherein the restriction endonuclease recognition site is recognized by the thermoresistant or thermostable restriction endonuclease. In other preferred embodiments, endonuclease digestion is performed prior to amplification of the extracted nucleic acid fraction. In a preferred embodiment, the nucleic acid is derived from a nucleic acid encoding an oncogene or other tumor-associated DNA.

In additional preferred embodiments, the invention provides a method for detecting extracellular tumor-derived or tumor-associated nucleic acid in a plasma or serum fraction of a blood sample, for diagnosis, detection, monitoring, evaluation or treatment of a neoplastic or proliferative disease in an animal or a human comprising the additional steps of digesting the amplified nucleic acid fraction with an enzyme that specifically cleaves nucleic acid fragments in the fraction within the nucleotide sequence of said nucleic acid fragments, whereby enzymatic cleavage thereof is accomplished in a nucleic acid fragment derived from a wildtype allele of said nucleic acid that is not associated with a neoplastic or proliferative disease, and wherein enzymatic cleavage is not accomplished in a nucleic acid fragment derived from a mutant or variant allele that is associated with a neoplastic or proliferative disease; then specifically re-amplifying a portion of the amplified, digested nucleic acid that is not cleaved by the enzyme, to provide a re-amplified nucleic acid fraction substantially comprising an undigested nucleic acid that is associated with neoplastic or proliferative disease; and detecting the re-amplified nucleic acid fragment that is associated with neoplastic or proliferative disease in the re-amplified nucleic acid fraction. In this embodiment of the inventive method, the amplified DNA fragments from the extracellular DNA extracted from plasma or serum is cleaved with an enzyme, preferably a restriction enzyme, that specifically digests fragments amplified from wildtype alleles of a gene associated with a neoplastic or proliferative disease, and specifically does not cleave DNA fragments amplified from mutant alleles of a gene wherein the mutated allele is associated with a neoplastic or proliferative disease. In a preferred embodiment, the restriction endonuclease is a thermoresistant or thermostable endonuclease and digestion is performed simultaneously with amplification. In another preferred embodiment, digestion is performed with a thermoresistant endonuclease over the course of an amplification reaction, whereby wildtype forms of the amplified nucleic acid are specifically cleaved and rendered unamplified by the end of the digestion/amplification reaction. In a preferred embodiment, the nucleic acid is derived from a nucleic acid encoding an oncogene or other tumor-associated DNA.

In particularly preferred embodiments, an enzyme recognition site is specifically engineered into the oligonucleotide primers used for amplification to provide an enzyme recognition site in the wildtype allele but not in the mutant allele, as the result of the nucleotide sequence differences between the wildtype and mutant alleles. In preferred embodiments, the extracted nucleic acid is amplified using an amplification method selected from the group consisting of polymerase chain reaction, ligase chain reaction, branched DNA signal amplification, boomerang DNA amplification, Q-beta replication, transcription-based amplification, isothermal nucleic acid sequence based amplification, self-sustained sequence replication assay, strand displacement activation, cycling probe technology, and combinations or variations thereof.

Also provided by the methods of the invention are amplified fragments of extracellular tumor-associated nucleic acid as detected using the methods of the invention.

Particularly preferred embodiments of the invention comprise amplification of nucleic acid sequences derived from or related to p53, bcl-2 and bcl-2/IgH translocation species.

Preferably the method is provided wherein amplification is achieved using oligonucleotide primers that specifically amplify a nucleic acid associated with a neoplastic or proliferative disease, most preferably an oncogene. In additional preferred embodiments, the amplification primers comprise a nested or hemi-nested set of primers as understood in the art and described herein.

In preferred embodiments of the inventive methods, extracellular nucleic acid is extracted from blood plasma or serum using an extraction method including gelatin extraction; silica, glass bead, or diatom extraction; guanidine- or guanidinium-based extraction; chemical extraction methods; and size-exclusion and anion-exchange chromatographic methods. In preferred embodiments, detection of the amplified DNA is performed using a detection method including gel electrophoresis; immunological detection methods; hybridization using a specific, fluorescent-, radioisotope-, antigenic- or chromogenically-labeled probe; Southern blot analysis; electrochemiluminescence; reverse dot blot detection; and high-performance liquid chromatography.

The methods of the invention are provided as diagnostic methods for detecting tumor-associated extracellular nucleic acid in a human at risk for developing a neoplastic or proliferative disease (whether the risk is recognized or unrecognized), comprising the steps of purifying extracellular nucleic acid from a plasma or serum fraction of a blood sample from the human to prepare a homogeneous preparation of extracted nucleic acid; specifically amplifying a portion of the extracted nucleic acid to provide an amplified nucleic acid fraction substantially comprising a nucleic acid that is associated with neoplastic or proliferative disease; and detecting the amplified nucleic acid fragment that is associated with neoplastic or proliferative disease in the amplified nucleic acid fraction. The detected fragment is then identified, e.g., as comprising the wildtype and mutated forms of an oncogene associated with a neoplastic or proliferative disease. In a preferred embodiment, the diagnostic methods of the invention are used to evaluate response of a human with a neoplastic or proliferative disease to a treatment regime or modality. In another preferred embodiment, the method is used to evaluate disease progression in a human. Additionally, the methods of the invention are preferably used to determine disease prognosis in a human. In other preferred embodiments, the methods of the invention are used to detect the presence of residual disease in a human following a course of treatment or after clinical tumor regression, or to detect actual or imminent clinical relapse.

Also provided as embodiments of the methods of the invention are methods additionally comprising the steps of determining the nucleic acid sequence of the nucleic acid fragment of extracellular nucleic acid that is associated with neoplastic or proliferative disease in the amplified nucleic acid fraction, wherein the nucleic acid sequence of the nucleic acid fragment comprising a mutated or variant allele of a nucleic acid associated with a neoplastic or proliferative disease.

In addition to the diagnostic methods noted above, the invention provides methods for isolating extracellular tumor-derived or tumor-associated nucleic acid from a fraction of a blood sample comprising the plasma fraction or the serum fraction of the blood sample. In these embodiments the method comprises the steps of purifying extracellular nucleic acid from plasma or serum to prepare a homogeneous preparation of extracted nucleic acid using a rapid extraction method; specifically amplifying a portion of the extracted nucleic acid to provide an amplified nucleic acid fraction substantially comprising a nucleic acid that is associated with neoplastic or proliferative disease; and cloning the amplified nucleic acid fragment that is associated with neoplastic or proliferative disease in the amplified nucleic acid fraction. Also provided in this aspect of the invention are recombinant genetic constructs comprising a nucleic acid fragment that is associated with neoplastic or proliferative disease prepared using the methods of the invention. Ribonucleic acid transcribed from the recombinant genetic constructs of the invention are also provided, as well as protein produced from translation of said RNA, and methods for using the translated proteins and peptides of the invention as epitopes for the production of antibodies and vaccines.

In preferred embodiments, the nucleic acid associated with neoplastic or proliferative disease is derived from an oncogene, most preferably wherein the oncogene is ras, p53, bcl-2 or the bcl-2/IgH translocated gene.

The invention also provides methods for detecting any nucleic acid in a sample for which oligonucleotide amplification primers are available. The invention provides a method for detecting a nucleic acid in a biological sample, the method comprising the steps of specifically amplifying a portion of the nucleic acid in the presence of a thermoresistant or thermostable endonuclease to provide an amplified nucleic acid fraction substantially comprising an amplified nucleic acid fragment; and detecting the amplified nucleic acid fragment. In a preferred embodiment, the nucleic acid is amplified using an amplification method selected from the group consisting of polymerase chain reaction, ligase chain reaction, branched DNA signal amplification, boomerang DNA amplification, Q-beta replication, transcription-based amplification, isothermal nucleic acid sequence based amplification, self-sustained sequence replication assay, strand displacement activation, cycling probe technology, and combinations or variations thereof. In a preferred embodiment, detection of the amplified DNA is performed using a detection method selected from the group consisting of gel electrophoresis, immunological detection methods, nucleic acid hybridization using a specific, fluorescent- or chromogenically-labeled probe, Southern blot analysis, electrochemiluminescence, reverse dot blot detection, and high-performance liquid chromatography. Nucleic acid from any biological source, including but not limited to eukaryotic, prokaryotic, viral and fungal nucleic acid, can be detected using the inventive method.

It is therefore the object of this invention to detect or infer the presence of cancerous or precancerous cells from non-hematologic or hematologic malignancies, within a human or animal body having recognized neoplastic disease or in those not previously diagnosed, by examining the plasma or serum fraction of blood for extracellular mutated oncogene DNA or tumor-derived or associated extracellular DNA, using a nucleic acid amplification assay, including but not limited to polymerase chain reaction (PCR), ligase chain reaction, branched DNA signal amplification assays, isothermal nucleic acid sequence based amplification (NASBA), other self-sustained sequence replication assays, transcription-based amplification, boomerang DNA amplification, strand-displacement activation, cycling probe technology, or combinations of such amplification methods, most preferably in the presence of a restriction endonuclease that specifically cleaves wildtype forms of tumor-derived or associated extracellular nucleic acid.

Another object of this invention is to detect or infer the presence of cancerous cells anywhere within a human or animal body by examining the plasma or serum fraction of peripheral blood of the organism for extracellular DNA containing mutant oncogene DNA or tumor-associated DNA, using one or several restriction endonucleases to separate wild-type oncogenes from mutant oncogenes and/or to enrich for mutant DNA, both in organisms known to have cancer and in those not previously diagnosed.

Another object of this invention is to rapidly extra extracellular DNA from plasma or serum.

An advantageous application of this invention is to identify, either quantitatively or qualitatively, mutant oncogenes or tumor-associated DNA in the blood plasma or serum of humans or animals during or following surgery to remove a premalignant lesion or a cancer, to classify such patients for their risk of residual cancer or metastasis following the surgery.

Another advantageous application of this invention is to identify, either quantitatively or qualitatively, mutant oncogenes or tumor-associated DNA in the blood plasma or serum of humans or animals who are receiving cancer therapies, including but not limited to chemotherapy, biotherapy, or radiotherapy, as a guide to whether adequate therapeutic effect has been achieved or whether additional or more advanced therapy is required, and to assess prognosis in these patients.

Another advantageous application of this invention is to identify, either quantitatively or qualitatively, mutant oncogenes or tumor-associated DNA in the blood plasma or serum of humans or animals who have completed therapy as an early indicator of relapsed cancer, impending relapse or treatment failure.

Another advantageous application of this invention is to identify, either by detection or inference, the presence of premalignant neoplasms through detection of mutant oncogenes or tumor-associated DNA in the blood of humans or animals when that mutant DNA derives from premalignant growths such as dysplasias or adenomas, or from other cells bearing a mutated oncogene. In addition, the invention advantageously provides a panel of several oncogene assays that can distinguish malignant from premalignant conditions, or assist in medical monitoring to detect transformation of the growth to an outright malignancy, or to detect regression. Furthermore, the invention advantageously provides a means to define risk of malignancy in a human wherein the risk was previously unrecognized.

Thus, the invention provides a method of screening both healthy individuals and individuals at risk for cancer and premalignant conditions.

Another advantageous application of this invention is to identify, either quantitatively or qualitatively, mutant oncogenes or tumor-associated DNA in the blood plasma or serum of humans or animals either newly or recently diagnosed with cancer or a premalignant condition in order to clarify when to initiate therapy, including adjuvant therapies.

Another advantageous application of this invention is to identify, either quantitatively or qualitatively, more than one mutant oncogene or tumor-associated DNA in the blood plasma or serum of humans or animals by use of a panel of DNA enrichment methods or by multiplex amplifications of mutant DNAs. Additional, said multiplex amplifications or collection of individual amplifications of mutant DNAs are provided to identify specific tumor types from the number and kind of oncogenes or other tumor-associated mutated DNAs detected.

Another useful application of this invention is to identify mutant oncogenes or tumor-associated DNA, either singly, multiplexed or using a panel of amplification reactions, in the blood plasma or serum of humans or animals in order to determine specific tumor characteristics for a given patient, to assist in the development of patient-specific therapies, or to help place a patient into a particular treatment regime or to help predict prognosis or tumor behavior.

Specific preferred embodiments of the present invention will become evident from the following more detailed description of certain preferred embodiments and the claims.

DETAILED DESCRIPTION OF THE INVENTION

Figure 1:
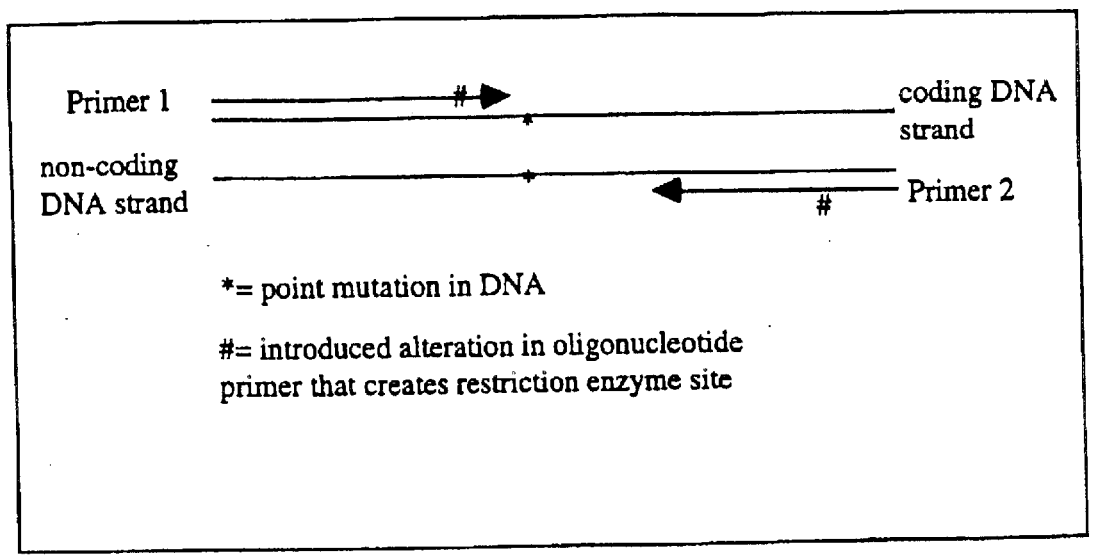
FIG. 1 shows a schematic diagram of the primer construction strategy for creating diagnostic restriction enzyme digestion sites in PCR amplified DNA fragments.

This invention provides methods for detecting or inferring the presence of cancerous or precancerous cells in a human or animal. The methods of the invention comprise means of extracting extracellular DNA from blood plasma or serum in a first step, separating mutated DNA from non-mutated, normal DNA by way of a discriminating restriction endonuclease digestion in a second step, and selectively amplifying and detecting the DNA in a third step, wherein amplification and detection can be performed either qualitatively or quantitatively. The second step may be combined with the third step using a thermostable restriction endonuclease, whereby amplification and digestion/selection are performed in a single step; this embodiment of the reaction being designated herein as combined amplification and restriction digestion (CARD) assay. This specification describes several methods that can be employed for the first step (rapid extraction of mutant DNA from plasma or serum). Similarly, the invention can amplify extracted mutant DNA in the third step by using any of several methods of nucleic acid amplification and their variations, including but not limited to polymerase chain reaction, ligase chain reaction, branched DNA signal amplification, isothermal nucleic acid sequence based amplification (NASBA), other self-sustained sequence replication assays, transcription-based amplification, boomerang DNA amplification, strand-displacement activation, cycling probe technology, and combinations of such amplification methods. Specific and detailed descriptions of several step one methods (rapid extraction of DNA from serum or plasma) and of several step three methods (nucleic acid amplification of mutant DNA) are given below as a description of the invention. However, it is emphasized that with this invention any of the described rapid DNA extraction steps may be used with any nucleic acid amplification assay that differentiates mutant DNA or amplifies DNA to achieve the objectives specified above.

Moreover, the assays and methods of the invention can be performed qualitatively, whereby the amount of the nucleic acid product produced is at least sufficient for efficient detection of the product, or quantitatively, whereby the amount of the nucleic acid product produced is measured with reference to a standard useful in determining the significance of the amount of produced nucleic acid (for example, wherein the amount of nucleic acid product is related to a disease state or risk of developing a disease state).

Specifically, the invention provides methods for detecting nucleic acid in plasma or serum of a human or animal wherein the nucleic acid is associated with the existence of pre-malignant cells or tissues in the human or animal, thereby providing a sensitive diagnostic means for early detection of neoplasia.

A General Overview of the Inventive Methods

In the practice of the invention blood is drawn by standard methods into a collection tube, preferably comprising siliconized glass, either without anticoagulant for preparation of serum, or with EDTA, sodium citrate, heparin, or similar anticoagulants, most preferably EDTA, for preparation of plasma. The preferred method, although not absolutely required, is that plasma or serum be fractionated from whole blood. First, this reduces the burden of extraneous intracellular DNA being extracted from non-malignant cells which might reduce the sensitivity of the amplification assay or interfere with the amplification assay through release of inhibitors such as porphyrins and hematin. Second, this prevents confounding variables introduced by intracellular DNA derived from circulating cancer cells, for example on interpretation of quantitative amplification studies. Plasma or serum may be fractionated from whole blood by centrifugation, preferably gentle centrifugation at 300–800×g for 5–10 minutes, or fractionated by other standard methods. However, high-speed centrifugation is avoided, as subjecting blood to such treatment may deplete the plasma or serum fraction of extracellular DNA. Since heparin may interfere with PCR, use of heparinized blood may require pretreatment with heparinase. Thus, EDTA is the preferred anticoagulant for blood specimens in which PCR amplification is planned. Either freshly-collected blood plasma or serum, or frozen (stored) and subsequently thawed plasma or serum can be used in the methods of the invention. Stored plasma or serum should be kept at −20° C. to −70° C., and freshly-collected plasma or serum kept refrigerated or maintained on ice until use.

Step One: Rapid Extraction of Extracellular DNA from Plasma or Serum

I. Gelatin Extraction Method:

In a preferred embodiment, DNA is co-precipitated from plasma or serum with gelatin by a method modified from that of Fournie et al. (1986, *Anal. Biochem.* 158: 250–256). A stock 5% (w/v) gelatin solution is prepared by mixing 1 gram gelatin (G8-500, Fisher, Pittsburgh, Pa.) with 20 mLs sterile, double-distilled water, autoclaving for 30 minutes, and filtering through a 0.2 micron filter. The resultant solution is sequentially frozen in a dry ice/ethanol bath and thawed at room temperature for a total of five cycles. A working 0.3% gelatin solution is prepared by heating the stock solution to 60° C. and mixing 600 μL of 5% gelatin with 25 μL of 1 M-Tris-HCl (pH 8.0) and 9.4 mLs of sterile, double-distilled water.

Plasma or serum (160 μL) is mixed with 12.8 μL of 0.5 M EDTA and 467 μL of sterile, double-distilled water, then emulsified for 3 minutes with 320 μL of phenol or phenol:chloroform:isoamyl alcohol (25:24:1 ratio). The solution is centrifuged at 14,000×g for 10 minutes, and 570 μL of the aqueous layer is removed to a clean tube. DNA is precipitated by addition of 142 μL of the 0.3% gelatin working solution and of 500 μL of cold absolute ethanol, followed by incubation at −20° C. for 1–2 hours. Extracellular DNA may be precipitated within less than 1 h of incubation at −20° C., and a very short incubation may be preferable in some circumstances. Alternatively, longer incubation at −20° C. for 1–2 hours insures the precipitation of most DNA. The sample is centrifuged at 14,000×g at 4–6° C. for 15 minutes, washed once with cold 70% ethanol, and dried in a 60° C. heat block for 10 minutes. DNA is then recovered by the addition of 35 to 70 μL of sterile, double-distilled water preheated to 60° C. Thirty-five μL of the resuspended DNA is used in either step two or step three.

II. Glass Bead, Silica Particle, or Diatom Extraction Method.

As an alternative rapid method of extracting extracellular DNA from plasma or serum, glass beads, silica particles, or diatoms may be used, as in the method or adaptation of Boom et al. (Boom et al., 1991, *J. Clin. Microbiol.* 29: 1804–1811; Boom et al., 1989, *J. Clin. Microbiol.* 28: 495–503). Size fractionated silica particles are prepared by suspending 60 grams of silicon dioxide ($SiO_2$, Sigma Chemical Co., St. Louis, Mo.) in 500 mLs of demineralized sterile double-distilled water. The suspension is then settled for 24 hours at room temperature. Four-hundred thirty (430) mLs of supernatant is removed by suction and the particles are resuspended in demineralized, sterile double-distilled water added to a final volume of 500 mLs. After an additional 5 hours of settlement, 440 mLs of the supernatant is removed by suction, and 600 μL of HCl (32% wt/vol) is added to adjust the suspension to a pH2. The suspension is aliquotted and stored in the dark.

Lysis buffer is prepared by dissolving 120 grams of guanidine thiocyanate (GuSCN, Fluka Chemical, Buchs, Switzerland) into 100 mLs of 0.1 M Tris hydrochloride (Tris-HCl) (pH 6.4), and 22 mLs of 0.2 M EDTA, adjusted to pH 8.0 with NaOH, and 2.6 grams of Triton X-100 (Packard Instrument Co., Downers Grove, Ill.). The solution is then homogenized.

Washing buffer is prepared by dissolving 120 grams of guanidine thiocyanate (GuSCN) into 100 mLs of 0.1 M Tris-HCl (pH 6.4).

Fifty μL of plasma or serum are mixed with 40 μL of silica suspension prepared as above, and with 900 μL of lysis buffer, prepared as above, using an Eppendorf 5432 mixer over 10 minutes at room temperature. The mixture is then centrifuged at 12,000×g for one minute and the supernatant aspirated and discarded. The silica-DNA pellet is then washed twice with 450 μL of washing buffer, prepared as above. The pellet is then washed twice with one mL of 70% (vol/vol) ethanol. The pellet is then given a final wash with one mL of acetone and dried on a heat block at 56 degrees centigrade for ten minutes. The sample is eluted for ten minutes at 56 degrees centigrade with a TE buffer consisting of 10 mM Tris-HCl, one mM EDTA (pH 8.0) with or without Proteinase K (100 ng/ml) as described by Boom et al. Following elution, the sample is then centrifuged at 12,000×g for three minutes, and the DNA-containing supernatant recovered. The DNA extract is now used in amplification. (Boom et al., 1991, ibid.; Boom et al., 1989, ibid.; Cheung et al., 1994, *J. Clin. Microbiol.* 32: 2593–2597).

III. Acid Guanidinium Thiocyanate-phenol-chloroform Extraction Method.

As an alternative method, extracellular DNA may be extracted from plasma or serum in step one using variations of the acid guanidinium thiocyanate-phenol-chloroform extraction method. For example, extracellular DNA may be extracted from plasma or serum using TRI reagent, a monophase guanidine-thiocyanate-phenol solution, as described by Chomczynski (1993, *Biotechniques* 15: 532–534). One mL of plasma or serum is processed using 5–10 mLs of TRI Reagent™ (TRI Reagent, Molecular Research Center, Cincinnati, Ohio, Trisolv™, BioTecx Laboratories, Houston, Tex., TRIzol™, GIBCO BRL/Life Technologies, Gaithersburg, Md., ISOGEN™, Nippon Gene, Toyama, Japan, RNA Stat™ 60, Tel-test, Friendsword, Tex.) according to manufacturer's directions. DNA is precipitated from the interphase with ethanol.

IV. Additional Nucleic Acid Extraction Methods

Alternate means of purification which may be used to obtain DNA from serum or plasma, including selective retention on a size exclusion column or similar matrix, salting-out method, and other guanidinium thiocyanate extraction methods known in the art.

Combined Amplification and Restriction Digestion (CARD)

The invention provides a particularly preferred embodiment comprising a combined amplification and restriction digestion step, termed CARD assay. This method allows the simultaneous performance of enrichment for mutant DNA (Invention Step two, described below) with amplification (invention Step three, described below), significantly shortening analysis time and reducing reagent consumption. The method relies upon the use of a thermoresistant or thermostable restriction endonuclease which is able to withstand elevated temperatures (>50° C.) for a prolonged period of time (>5–10 minutes). Thermostable restriction enzymes generally have reaction conditions similar to those of thermostable DNA polymerase, so that both enzymes may function simultaneously in the same reaction container. The only criterion for use of the CARD method is that wild-type oncogene DNA carry a thermostable restriction enzyme recognition site that is altered in mutant oncogene DNA. If such a site does not exist naturally, oligonucleotide primers may be designed to flank the site of mutation and create a restriction site by altering one or more bases (see FIG. 1). Thus, this method has broad application to the rapid selection of mutant oncogene molecules from a mixture or background of non-mutant oncogene molecules. Indeed, this method may be applied to other settings, not limited to oncogene DNA detection, in which one form or sequence of DNA is to be selected—on the basis of the presence or absence of a restriction enzyme site—from another form or sequence of DNA.

The preferred embodiment of CARD is performed as follows:

DNA is prepared using any of the means described in invention step 1. A mixture of 35 µL of plasma or serum DNA, 50 mM potassium chloride, 10 mM Tris-HCl (pH 9.0), 0.1% Triton X-100, 1.5 mM magnesium chloride, 200 micromolar each dATP, dCTP, dGTP, dTTP, 15 picomole each oligonucleotide (Primers 1 and 2)(the precise amount of each oligonucleotide primer may vary empirically from one target DNA to another), 4 units thermostable restriction endonuclease (the precise amount of each restriction enzyme may vary depending on its degree of thermostability, with more being needed for relatively labile enzymes), and 1 unit Taq polymerase (Promega, Madison, Wis.) is prepared in a volume of 50 µL.

In the preferred embodiment, the polymerase chain reaction mixture is incubated at 94° C. for 7 seconds, then at 55–60° C. (depending on the degree of thermostability of the restriction enzyme and annealing temperature of the oligonucleotide primers) for 3 minutes, then at 94° C. for 6 seconds, again annealed, extended and digested at 55–60° C. for 3 minutes, then incubated at 94° C. for 5 seconds, and so on, decreasing the length of 94° C. denaturation by one second each cycle until after 6 rounds the denaturation lasts only 1 second. Thereafter, cycles with one second denaturation steps and 3 minute extension and digestion steps are performed until a total of 40 is reached. After cycle 10, the reactions are paused at 60° C. and an additional 10 units of restriction enzyme are added to each tube.

At the completion of the temperature cycling, twenty-five µL of the polymerase chain reaction (PCR) mixture is then removed to a new tube and mixed with restriction enzyme reaction buffer and 10 units of the chosen restriction enzyme in a volume of 30 µL, then incubated at the appropriate temperature for reaction to occur for 90 minutes. A second aliquot is added and the reaction continued for 90 minutes more prior to proceeding to any method of detection specified in invention step three. Alternatively, at the completion of temperature cycling, 10U of the chosen restriction enzyme are added directly to the cycling reaction tube and this mixture incubated at the appropriate temperature for 1–2 h prior to commencement of the detection step.

The CARD amplification method is also applicable to detecting any nucleic acid in any biological or other sample, wherein amplification primers for the nucleic acid of interest are known or may be derived, and in which a restriction enzyme digestion site recognized by a thermoresistant or thermostable restriction endonuclease is present or can be created using the methods of the invention. The use of the CARD method of the invention is exemplified but not limited to detection of extracellular tumor-derived or tumor-associated nucleic acid herein.

Step Two: Enrichment for Mutant DNA

Following extraction of extracellular DNA from plasma or serum in step one, the DNA is amplified using a nucleic acid amplification assay. One or more of several amplification assays may be used, including polymerase chain reaction, ligase chain reaction, branched DNA signal amplification, isothermal nucleic acid sequence based amplification (NASBA), other self-sustained sequence replication assays, transcription-based amplification, boomerang DNA amplification, strand-displacement activation, cycling probe technology, or combinations of amplification methods such as polymerase chain reaction combined with ligase detection reactions. The sensitivity of some amplification assays may be increased by invention step two, which is an optional step, whereby mutant DNA is enriched through the use of a restriction enzyme, as adapted from the method of Kahn et al. (Kahn et al., 1991, ibid.).

A restriction endonuclease is chosen to examine one portion of a known oncogene or tumor-associated DNA for mutations. Restriction endonucleases are naturally occurring enzymes with the ability to recognize a particular arrangement of nucleotide bases and, with absolute specificity, to cleave double stranded DNA at or near the site of recognition. Oncogenes such as p53, p16, BRCA1 and ras exhibit a number of alterations in their DNA sequence that can be identified on the basis of altered restriction enzyme recognition and cleavage. The second step of the invention uses cleavage of normal, non-mutated oncogene DNA by a restriction endonuclease chosen to span one or more of the nucleotides known to be mutated with some frequency in cancers and their precursors. DNA can then be amplified by any of several methods including but not limited to the polymerase chain reaction, the ligase chain reaction, self-sustaining sequence replication and others. Since wild-type DNA has been selectively cleaved by restriction endonuclease digestion, and cleavage prevents DNA amplification, mutant oncogene DNA is relatively enriched following the amplification stage. This cycle of cleavage and amplification may be repeated to further enrich the test sample for mutant DNA.

If no restriction enzyme recognition site can be located from an examination of the known sequence of the oncogene under study, such a site may be created by the introduction of a new base into the sequence during a preliminary round of DNA amplification. This method is illustrated in the Example provided below.

In the preferred embodiment, if no restriction enzyme site exists, a preliminary round of DNA amplification is performed as follows. A pair of oligonucleotide primers, each 20–30 nucleotides long, is manufactured to be complementary to the oncogene being examined (see FIG. 1). One of the primers (Primer 1) is designed to lie immediately adjacent to the location where mutation occurs in neoplasia. Restriction enzyme sites are introduced into each of the primers by changing one or two nucleotides as necessary. Primer 1 is altered so that only non-mutated, wild-type DNA is cleaved. Primer 2 is altered to introduce a site recognized by the same restriction enzyme, which serves as an internal control for digestion.

Primers used in CARD assay or in invention steps two and three should be based on the specific tumor-derived or associated DNA of interest which characterizes the tumor. Tumor-derived or associated DNA includes but is not limited to:

DNA related to mutated oncogenes or other mutated DNA, a partial list of which includes H-ras, K-ras, N-ras, c-myc, her-2/neu, bcr-abl, fms, src, fos, sis, jun, bcl-2, bcl-2/IgH, or VHL (Von Hippel-Lindau gene)

DNA related to tumor suppressor genes, a partial list of which includes p53, RB, MCC, APC, DCC, NF1, WT1.

DNA related to tumor-associated protein which is found elevated in certain cancers, a partial list of which includes alpha-fetoprotein (AFP), carcinoembryonic antigen. (CEA), TAG-72, CA 19-9, CA-125, prostate specific antigen (PSA), epidermal growth factor receptor, and epidermal growth factor DNA related to tumor-derived protein not normally found circulating in blood, a partial list of which includes tyrosinase DNA, keratin 19 DNA DNA related to tumor-specific antigens, such as MAGE 1, MAGE 2, MAGE 3, MAGE 4 and MAGE 4

For example, for mutant K-ras oncogene DNA, oligonucleotide K-ras. primers can consist of:
K-ras primer 1
5'-ACTGAATATAAACTTGTGGTAGTTGGACCT-3' (SEQ ID. No.:1)
K-ras primer 2
5'-TCAAAGAATGGTCCTGGACC-3' (SEQ ID No.:2).

The oligonucleotide K-ras primer 1 is immediately upstream of codon 12, and modified at the 28th base (G→C) to create an artificial restriction enzyme site (BstNI) The oligonucleotide K-ras primer 2 is modified at the 17th nucleotide (C→G) to create an artificial BstNl site to serve as an internal control for completion of digestion. The amplified mutant K-ras product is of 142 base pair length.

In another example, oligonucleotide p53 primers specific for mutant alleles of the p53 oncogene are shown below in Tables I and II. Specifically, different primers may be utilized in methods of the invention comprising two amplification steps, allowing for "nesting" or "hemi-nesting" of the amplification products to provide greater specificity and decrease the amount of analysis required to detect the amplified product. An example of sets of hemi-nested primers are shown in Tables II and III for mutant p53 oncogene DNA.

In another example, the bcl-2 oncogene DNA, oligonucleotide bcl-2 primers can consist of:

```
MBR       5'-TTAGAGAGTTGCTTTACGTG-3'  (SEQ ID No.:3)
J_HCON    5'-ACCTGAGGAGACGGTGACC-3'   (SEQ ID No.:4)
MBR-int   5'-GCCTGTTTCAACACAGACC-3'.  (SEQ ID No.:5)
```

In a preferred embodiment, polymerase chain reaction is performed as a two part amplification, in which enrichment of mutant DNA with the restriction enzyme is performed following the first amplification. However, as an alternative to polymerase chain reaction other amplification methods or their variants may be used, as noted herein.

In a preferred embodiment, a polymerase chain reaction mixture consisting of 35 µL of DNA from serum or plasma, 50 mM potassium chloride, 10 mM Tris-HCl (pH 9.0), 0.1% Triton X-100, 1.5 mM magnesium chloride, 200 micromolar each dATP, dCTP, dGTP, dTTP, 0.5 picomole each oligonucleotide (Primers 1 and 2)(the precise amount of each oligonucleotide primer may vary empirically from one target DNA to another), and 1 unit Taq polymerase (Promega, Madison, Wis.) is prepared in a volume of 50 µL.

In a preferred embodiment, the polymerase chain reaction mixture is cycled 15–20 times at 94° C. for 48 seconds, 56° C. for 90 seconds, and 72° C. for 155 seconds in an automated thermocycler (Ericomp Deltacycler or similar), as adapted from Kahn (1991, ibid,), prior to restriction enzyme enrichment of DNA.

Ten µL of the polymerase chain reaction (PCR) mixture is then removed to a new tube and mixed with restriction enzyme reaction buffer and 10 units of the chosen restriction enzyme in a volume of 20 µL, then incubated at the appropriate temperature for reaction to occur for 90 minutes. A second aliquot of enzyme is added and the reaction continued for 90 minutes more prior to proceeding to step three.

Step Three: Nucleic Acid Amplification and Detection

Extracellular DNA which has been extracted from plasma or serum during step one, is amplified by a nucleic acid amplification assay utilized for detection of low numbers of DNA molecules. Applicable assays include polymerase chain reaction (PCR), ligase chain reaction, branched DNA signal amplification, isothermal nucleic acid sequence based amplification (NASBA), other self-sustained sequence replication assays, transcription-based amplification, Q-beta replication, boomerang DNA amplification, strand-displacement activation, cycling probe technology, and combinations of such amplification methods.

Primers used in the amplification assay should be based on the specific tumor-derived or associated DNA or mutant oncogene DNA of interest which characterizes the tumor, as has been previously described and characterized herein (see step two).

I. Polymerase Chain Reaction Amplification:

Amplification reaction specifics using CARD assay are as described above, Otherwise, 10 µL of the digested PCR mixture from step two is removed to a new tube and constituents for another PCR reaction are added in a volume of 50 µL. All constituents are identical to those in step two except that 15-fold more of each oligonucleotide primer is used. The same cycling conditions are employed for 35 cycles. Alternatively, if invention step two is omitted, an amplification reaction is prepared using 35 µL of plasma or serum in a final volume of 50 µL, with remaining constituents as for the preferred version of step three, with the preferred PCR amplification performed in an automated thermocycler for 15–30 cycles at 94° C. for 48 seconds, 56° C. for 90 seconds and 72° C. for 155 seconds per cycle (parameters may be varied and are advantageously optimized for each primer pair).

Following completion of thermocycling, twenty-five μL of this PCR reaction are removed to a new tube, and constituents are added for a second restriction digestion with the same enzyme. Seventeen units of enzyme are added in a final volume of 35 μL, with all other constituents as in the first digestion. The reaction is performed for 60 minutes, followed by addition of 10 additional units of restriction enzyme and digestion for an additional 60 minutes. The amplified PCR product is then detected as described herein (see Detection).

If a restriction enzyme site is already present at the point of oncogene mutation, Primer 1 need not contain any mismatches with the known oncogene sequence and may be placed any convenient distance from the point mutation site under examination. Primer 2, however, should still be constructed to contain a restriction site cleavable by the same enzyme to serve as an internal control. In all instances, the PCR products should be no larger than 150–200 base pairs, any sequence change introduced into Primer 1 should be as far from the three prime end as possible, and the sequence change in Primer 2 should create a site that cleaves approximately 10 base pairs from its five prime end. For further clarification, see Example 1 in which a preferred embodiment is used for detection of extracellular mutant K-ras oncogene DNA in plasma or serum.

Other variations of polymerase chain reaction, including quantitative PCR, for example as adapted to the method described by Wang et al. (1989, *Proc. Natl. Acad. Sci. USA* 86: 9717–9721) or by Karet et al. (1994, *Anal. Biochem.* 220: 384–390), may alternatively be used.

II. Ligase Chain Reaction Amplification:

Other methods of DNA amplification including ligase chain reaction, and others as described herein that specifically create new DNA can be employed with the same effect. The ligase chain reaction (LCR), which uses a thermostable ligase enzyme to create new double-stranded DNA fragments out of 4 closely apposed oligonucleotides, can be used either qualitatively or quantitatively to detect mutant oncogenes in blood as follows. Oligonucleotides are selected to lie directly upon the oncogene mutation site of interest. The 2 oligonucleotides that are complementary to the mutation site are manufactured to contain the mutant nucleotides only at their three prime ends, thus excluding hybridization to the non-mutated, wild-type oncogene. If a restriction site exists around the nucleotide(s) of interest; it may be used for restriction digestion to selectively cleave the wild-type molecules. Alternatively, if no restriction site exists one can be created by the introduction of sequence changes in the oligonucleotides. Finally, if adequate thermodynamic discrimination can be made between mutant and wild-type sequences by the hybridizing oligonucleotides (allele specific hybridization or amplification), no restriction digestions need be performed and detection of mutant oncogene DNA may proceed directly from the DNA harvesting step.

An example of the use of LCR in detection of oncogene DNA in plasma or serum, an assay for K-ras DNA mutated at codon 12 is illustrated. Following extraction of serum or plasma DNA as in step 1, a ligase chain reaction mixture consisting of 35 μL of DNA from serum or plasma, 20 mM potassium chloride, 20 mM Tris-HCl (pH 7.5), 0.1% NP-40, 10 mM magnesium chloride, 0.1 mM rATP, 1 mM dithiothreitol, 10 nanograms each of primers LCR1 (5'-ATTACTTGTGGTAGTTGGAGCTGA/T/C-3'; SEQ ID No.:6), where the last position is a mixture of three nucleotides A/T/C), LCR2 (5'-TGGCGTAGGCAAGAGTGC-3'; SEQ ID No.:7), LCR3 (5'-GCACTCTTGCCTACGCCAA/G/T-3' (SEQ ID No.:8), where the last position is a mixture of three nucleotides A/G/T), LCR4 (5'-CAAGCTCCAACTACCACAAGTAAT-3'; SEQ ID No.:9), and 1 unit Pfu DNA ligase (Stratagene, La Jolla, Calif.) is prepared in a volume of 50 μL. The ligase chain reaction mixture is incubated at 92° C. for 4 minutes, followed by 60° C. for 3 minutes, then is cycled 20–25 times at 92° C. for 20 seconds and 60° C. for 20 seconds in an automated thermocycler (Ericomp Deltacycler or similar). This reaction mixture is then used in one or more detection assays as described in step three. This ligation chain reaction depends upon the ability of the ligase enzyme to join two DNA primers only if they match the target or template DNA (in this case, DNA extracted from serum or plasma) exactly, particularly at the three prime ends. The mixture of nucleotides at the three prime ends of LCR1 and LCR3 will recognize any mutant at the second position of the twelfth codon, and will effectively amplify it. By contrast, the wild type sequence will not hybridize effectively with these primers, ligation will not occur, and there will be no amplification of wild type DNA.

III. Alternative Methods of Nucleic Acid Amplification:

An alternative method of either qualitative or quantitative amplification of nucleic acid which may be used in step three is branched DNA signal amplification, for example as adapted to the method described by Urdea et al. (1993, *AIDS* 7: S11–14; 1991, *Nuclic Acids Res. Symp. Ser.* 24: 197–200), modified as follows. Plasma or serum are subjected to centrifugation at reduced speeds, as previously described, and extracellular DNA extracted as described herein in Step one above. Extracellular DNA is then applied directly to microwells and detection performed essentially as described, using target probes specific for the tumor-associated DNA of interest, whereby chemiluminescence is detected in amounts proportional to the amount of tumor-associated DNA present in the sample.

An alternative method of either qualitative or quantitative amplification of nucleic acid which may be used in step three is isothermal nucleic acid sequence based amplification (NASBA), for example as adapted to the method described by Kievits et al. (1991, *J. Virol. Methods* 35: 273–286) or by Vandamme et al. (1995, *J. Virol. Methods* 52: 121–132).

Alternative methods of either qualitative or quantitative amplification of nucleic acids which may be used in step three include Q-beta replication, other self-sustained sequence replication assays, transcription-based amplification, boomerang DNA amplification, strand-displacement activation, cycling probe technology, and combinations of amplification methods such as polymerase chain reaction combined with ligase detection reactions.

Following completion of amplification, the product is detected as described below.

IV. Detection of Amplified Product

There are numerous methods to detect amplified DNA, any of which may be used for detection of amplified product in step three.

In one method, amplified DNA product is detected in step three using gel electrophoresis. In the preferred embodiment, 25 μL of the second digestion product is electrophoresed through a 3% agarose gel in 1×TBE at 75 VDC for approximately 2 hours before staining with ethidium bromide. Mutant DNA is evident on the gel as a single band of length (PCR product length minus cleaved portion of Primer 2); failure of digestion is evident by a band the size of the full-length PCR product, while wild-type, non-mutated DNA is generally not evident but may sometimes be seen as a band at length (PCR product length minus cleaved portion of Primer 2 minus cleaved portion of Primer 1). As an alternative to ethidium bromide, the amplified product can be transferred from the gel to a membrane by blotting techniques such as Southern blot analysis to be detected with a labeled probe.

As an alternative means of detection of the mutant oncogene signal, any type of hybridization reaction or other method that separates different-sized PCR products may be employed. For example, an oligonucleotide complementary to the central portion of the PCR product may be bound to a matrix, and a separate oligonucleotide complementary to the five prime end of the PCR product, labeled with a fluorescent or chromogenic tag, can be used as a detector. With this format, only PCR products containing the uncleaved five prime end will hybridize and yield a signal. This approach lends itself to automation and to quantitation, since the fluorescent signal can be cumulated. Additionally, a fluorescent or other tag can be placed on Primer 1 prior to the thermocycling reaction and, with proper adjustment of cycling parameters, the intensity and thus quantity of mutant oncogene can be read directly following the second round of restriction digestion, as in the Taqman LS-50B PCR Detection System (Perkin-Elmer, Foster City, Calif.).

An alternative method which may be used in step three to detect the amplified DNA product is ELISA detection. Depending upon the ELISA detection method used, it may be necessary to biotinylate or otherwise modify the primers used in step three. For example, one ELISA detection method which may be used in step three is the method described by Landgraf et al. (1991, Anal. Biochem. 198: 86–91) as follows:

Primers are modified with biotinylamidocaproate-N-hydroxysuccinimidester (Sigma) and fluorescein isothiocyanate (FITC) (Sigma), by the method of Landgraf et al. (1991, Anal. Biochem. 193: 231–235). Following amplification the ELISA is carried out in microtiter plates coated with 1 microgram/mL affinity-purified avidin (13 U/mg, Sigma). One $\mu$L of the final amplification product (or post-digestion product) is diluted with 50 $\mu$L of PBS-Tween, and then incubated at room temperature for 30 minutes in the microtiter plate well. Non-incorporated primers are removed by washing with PBS-Tween. The plates are then incubated at room temperature for 30 minutes after adding 50 $\mu$L per well of anti-FITC antibody-HRPO conjugate (Dakopatts) which is at a 1:500 dilution with PBS-Tween. Following this, 80 $\mu$L of an ELISA solution made from one milligram 3, 3', 5, 5' tetramethylbenzidine (Sigma) dissolved in one mL dimethyl sulfoxide, and diluted 1:10 with 50 millimol sodium acetate:citric acid, pH 4.9, with 3 $\mu$L of 30% (vol/vol) $H_2O_2$ added, is added to each well. After 2–5 minutes, the reaction is stopped by adding 80 $\mu$L of 2M $H_2SO_4$. The optical density is then read at 450 nm.

Alternative methods of ELISA detection which may be used in step three include, but are not limited to, immunological detection methods using monoclonal antibody specific for RNA/DNA hybrids, such as by adapting methods described by Coutlee et al. (1989, Anal. Biochem. 181: 96–105), or by Bobo et al. (1990, J. Clin. Microbiol. 28: 1968–1973).

Alternative methods of ELISA detection which may be used in step three include, but are not limited to, commercial detection systems such as the SHARP signal system (Digene Diagnostics, Inc.), and the DNA enzyme immunoassay (DEIA), (GEN-ETI-K DEIA, Sorin Biomedica).

Alternative methods by which amplified product may be detected include but are not limited to all methods of electrochemiluminescence detection, such as by adapting the method described by Blackburn et al. (1991, Clin. Chem. 37: 1534–1539), or by DiCesare et al. (1993, Biotechniques 15: 152–157), all methods utilizing reverse dot blot detection technology and all methods utilizing high-performance liquid chromatography.

Finally, several separate assays examining different oncogenes or different regions of the same oncogene may be performed on the sample simultaneously, either in separate reaction tubes or, through judicious choice of oligonucleotides and restriction enzymes, in the same tube. This multiplexing approach allows greater sensitivity for detecting any single mutated oncogene and thus greater sensitivity for cancer detection. It may be that particular patterns of mutated oncogenes, yet to be identified, have particular clinical significance as to type of carcinoma present or prognosis.

Therapeutic Applications

The extraction of extracellular DNA from plasma or serum, and the amplification of tumor-associated or derived DNA to detectable levels, permits further analysis or other manipulation of that DNA, from which further clinical utility is realized. In this optional step of the invention, amplified extracellular DNA is analyzed to define the characteristics or composition of the tumor from which the DNA originates. Any of several methods may be used, dependent upon the desired information, including nucleic acid sequencing, spectroscopy including proton NMR spectroscopy, biochemical analysis, and immunologic analysis. In the preferred embodiment, amplified DNA is isolated—for example by excising mutant DNA bands from an agarose gel—reamplified, cloned into a plasmid vector, for example the pGEM-T vector plasmid (Promega) and sequenced using a commercial kit such as Sequenase 2.0 (USB). Analysis to define the characteristics or composition of the extracellular DNA, and thus the tumor of origin, affords a wide array of clinical utility, including the description, characterization, or classification of the tumor, whether known or occult, such as by tissue of origin, by type (such as premalignant or malignant), phenotype, and genotype, and by description or characterization of tumor behavior, physiology and biochemistry, as to gain understanding of tumor invasiveness, propensity to metastasize, and sensitivity or resistance to various therapies, thereby allowing the prediction of response to either ongoing or planned therapy and, further, allowing evaluation of prognosis. Comparison of the characteristics of extracellular DNA to previous biopsy or surgical specimens permits further evaluation of tumor heterogeneity or similarity in comparison to that specimen, and thus evaluation of tumor recurrence.

Following extraction of extracellular DNA from plasma or serum, complimentary ribonucleic acid (RNA) may be transcribed or manufactured from the DNA. In a preferred embodiment, transcription of RNA is performed by employing a primer with an RNA polymerase promoter region joined to the standard primer sequence for the DNA of interest in the amplification reaction (step three). RNA complimentary to the DNA is then transcribed from the attached promoter region. In an alternative method, amplified extracellular DNA is cloned into an expression vector, and RNA complimentary to the DNA is transcribed. Furthermore, as an optional preferred embodiment, the complimentary RNA is used in an in vitro translation reaction to manufacture tumor-associated or tumor-specific protein.

Extraction of extracellular DNA, amplification of tumor-derived or tumor-associated DNA, and characterization, transcription of complimentary RNA, and translation to tumor-associated or tumor-specific protein, provides significant utility, both in the assignment of therapy and in the development of tumor-specific therapies. Sequencing of extracellular DNA or transcription of complementary RNA allows assignment or development of antisense compounds, including synthetic oligonucleotides and other antisense constructs appropriately specific to the extracellular DNA, such as by construction of an expression plasmid such as by adapting the method of Aoki et al. (1995, *Cancer Res.* 55: 3810–3816). Similarly, defining tumor characteristics allows assignment of specific monoclonal antibody or vaccine therapies appropriately specific to the amplified DNA. Production of corresponding immunologic protein can be used in the development of tumor-specific monoclonal antibodies. Similarly, translated protein can be used in tumor-specific vaccine development. Furthermore, the extracellular DNA permits a means of defining or allowing the construction of a DNA construct which may be used in vaccine therapy.

Of particular value, the invention allows the development and application of these tumor-specific therapies even when only premalignant tumors, early cancers, or occult cancers are present. Thus, the invention allows therapeutic intervention when tumor burden is low, immunologic function is relatively intact, and the patient is not compromised, all increasing the potential for cure.

The invention also provides methods for transcribing RNA complementary to the isolated extracellular nucleic acid from plasma or serum, as well as methods for producing peptides and proteins (or fragments thereof) encoded thereby. Additional methods for using the peptide and proteins as antigens for producing antibodies specific for the peptides and proteins encoded by the extracellular nucleic acids of the invention are also provided. The isolated extracellular nucleic acids of the invention are also used in methods for producing antisense oligonucleotides, either synthetically or using recombinant genetic methods, and the use thereof for affecting gene expression in a cell will be appreciated by one having ordinary skill in the art in view of the methods for isolating and identifying said extracellular nucleic acid provided herein. Vaccine production, as is understood by one with skill in the art, is also enabled using the methods of the invention.

The methods of the invention and preferred uses for the methods of the invention are more fully illustrated in the following Examples. These Examples illustrate certain aspects of the above-described method and advantageous results. These Examples are shown by way of illustration and not by way of limitation.

EXAMPLE 1

Detection of Extracellular Mutant K-ras Oncogene DNA in Plasma or Serum

1. Background

Colorectal cancer (CRC) is a common and often fatal disease, representing the second or third leading cause of cancer death in the U.S. Local spread of disease is common, and regional or widespread metastasis has occurred in roughly 60% of CRC at the time of diagnosis (Parker et al., ibid.). Current screening tests for CRC involve stool sampling for occult blood or endoscopic examination. These methods provide no information on the spread of disease, however.

Advances in the understanding of the benign-to-malignant transformation sequence are based largely on studies of CRC and its precursors (Fearon et al., 1987, *Science* 238: 193–197; Fearon & Vogelstein, 1990, *Cell* 61: 759–767; Hamilton, 1992, *Cancer* 70: 1216–1221). The genesis of an adenocarcinoma is understood to require the occurrence of a number of mutational events, leading to the transformation of normal epithelium into a clonal malignancy. While no single event has been identified as being crucial to the development of CRC, mutation of the K-ras oncogene has been detected in 40–75% of all CRC and is found in roughly the same proportion of pre-malignant adenomas (Bos et al., 1987, *Nature* 327: 293–7; Yamagata et al., 1994, *Jap. J. Cancer Res.* 85: 147–51). K-ras mutation occurs in later stages of adenoma development and persists during the clonal transformation process (Vogelstein et al., 1988, *N. Engl. J. Med.* 319: 525–32). Mutations of K-ras, located on chromosome 12p, seem to play an important role in a number of malignancies. In CRC these mutations almost always are missense mutations confined to codons 12, 13 and 61, with the first in particular being common (Chaubert et al., 1994, *Amer. J. Path.* 144: 767–75; Kondo et al., 1993, *Cancer* 73: 1589–94; Oudejans et al., 1991, *Int. J. Cancer* 49: 875–9; Pellegata et al., 1992, *Anticancer Res.* 12: 1731–6; Sidransky et al., 1992, *Science* 256: 102–5). These mutations appear to alter the normal function of this proto-oncogene (Finney & Bishop, 1993, *Science* 260: 1524–7; Shirasawa et al., 1993, *Science* 260: 85–8).

2. Details of the Assay

This embodiment of the inventive assay was performed in the following steps.

Step one: Plasma or serum samples from six patients with advanced colorectal cancer and 15 normal volunteers were used in the assay. Extracellular DNA from plasma or serum samples was co-precipitated with gelatin using a modification of the method of Fournie et al. (1986, *Anal. Biochem.* 158: 250–6). Briefly, 160 $\mu$L plasma or serum was mixed with 12.8 $\mu$L 0.5 M EDTA and 467 $\mu$L sterile, double-distilled water, then emulsified for 3 minutes with 320 $\mu$L phenol or phenol:chloroform:isoamyl alcohol (25:24:1). The solution was centrifuged at 14,000×g for 10 minutes to resolve the aqueous and organic phases, and 570 $\mu$L of the aqueous layer was removed to a clean tube. DNA was precipitated by addition of 142 $\mu$L of a 0.3% gelatin solution prepared as described above and 500 $\mu$L of cold absolute ethanol, followed by incubation at −20° C. for 2 hours. The sample was centrifuged at 14,000×g at 6° C. for 15 minutes, washed once with cold 70% ethanol, and dried in a 60° C. heat block for 10 minutes. DNA was then recovered by the addition of 35 to 70 $\mu$L of sterile, double-distilled water preheated to 60° C. Thirty-five $\mu$L of the resuspended DNA was used in the second step of the assay.

Step two: DNA fragments specific for nucleic acid sequences of mutant K-ras oncogene in the isolated extracellular DNA preparation of Step One were amplified utilizing a non-radioactive PCR assay adapted from Kahn et al. (1991, *Oncogene* 6: 1079–1083) as follows. A reaction mixture was prepared containing 35 $\mu$L of the isolated extracellular DNA of Step One, 50 mM potassium chloride, 10 mM Tris buffer (pH 9.0), 0.1% Triton X-100, 1.5 mM magnesium chloride, 200 $\mu$M for each nucleoside triphosphate (dATP, dGTP, dCTP, and dTTP), 0.5 pmol oligonucleotide K-ras primer 1 having the sequence:

5'-ACTGAATATAAACTTGTGGTAGTTGGACCT-3' (SEQ ID No. 1), 0.75 pmol oligonucleotide K-ras primer 2 having the sequence:

5'-TCAAAGAATGGTCCTGGACC-3' (SEQ ID No.: 2), and 1U Taq DNA polymerase (Promega, Madison, Wis.)

in a final volume of 50 μL. Oligonucleotide K-ras primer 1 was constructed to contain the nucleotide sequence that is immediately upstream of mutant codon 12 (positions 99–128; Genbank Accession #L00045) of the K-ras gene, and is modified at the 28th base (G→C) to create a non-naturally-occurring restriction enzyme digestion site (BstNI). Oligonucleotide K-ras primer 2 is constructed to contain the nucleotide sequence complementary to the sequence of K-ras (at the complement of positions 255–236; Genbank Accession #L00045), and is modified at the 17th nucleotide (C→G) to create a non-naturally-occurring BstNI site that serves as an internal control to monitor restriction enzyme digestion. The reaction mixture was overlaid with mineral oil and thermocycled 15–20 times using a thermal profile of 94° C. for 48 seconds, 56° C. for 90 seconds, and 72° C. for 155 seconds in a PHC-2 thermocycler (Techne, Princeton, N.J.). Ten μL of the PCR mixture was then removed to a new tube and mixed with 1×BstNI reaction buffer and 10 units BstNI restriction enzyme (Stratagene, La Jolla, Calif.), and then incubated at 60° C. for 90 minutes. A second aliquot of 10 units BstNI was added and the reaction continued for an additional 90 minutes.

Step three: Ten μL of the digested PCR mixture was removed to a clean tube and a new reaction mixture was set up for the second round of amplification, using the same constituents as in the first amplification with the exception that 7.7 pmoles of oligonucleotide K-ras primer 1 and 11.5 pmoles of oligonucleotide K-ras primer 2 were used. The same cycling conditions were employed for 33–35 amplification cycles. A second BstNI restriction digestion was then performed using 25 μL of the second step PCR product and 17 units of enzyme in a final volume of 35 μL. Digestions were performed for 60 min at 60° C., followed by the addition of a second aliquot of 10U of enzyme and a digestion for an additional 60 min. The final digestion product was analyzed by gel electrophoresis on a 3% agarose gel (NuSieve, FMC Bioproducts, Rockland, Me.) in 1×TBE buffer at 75V DC for about 2 h and DNA fragments visualized by staining with ethidium bromide and ultraviolet light illumination (Foto-prep Transilluminator, Fotodyne, Hartland, Wis.).

Figure 2:
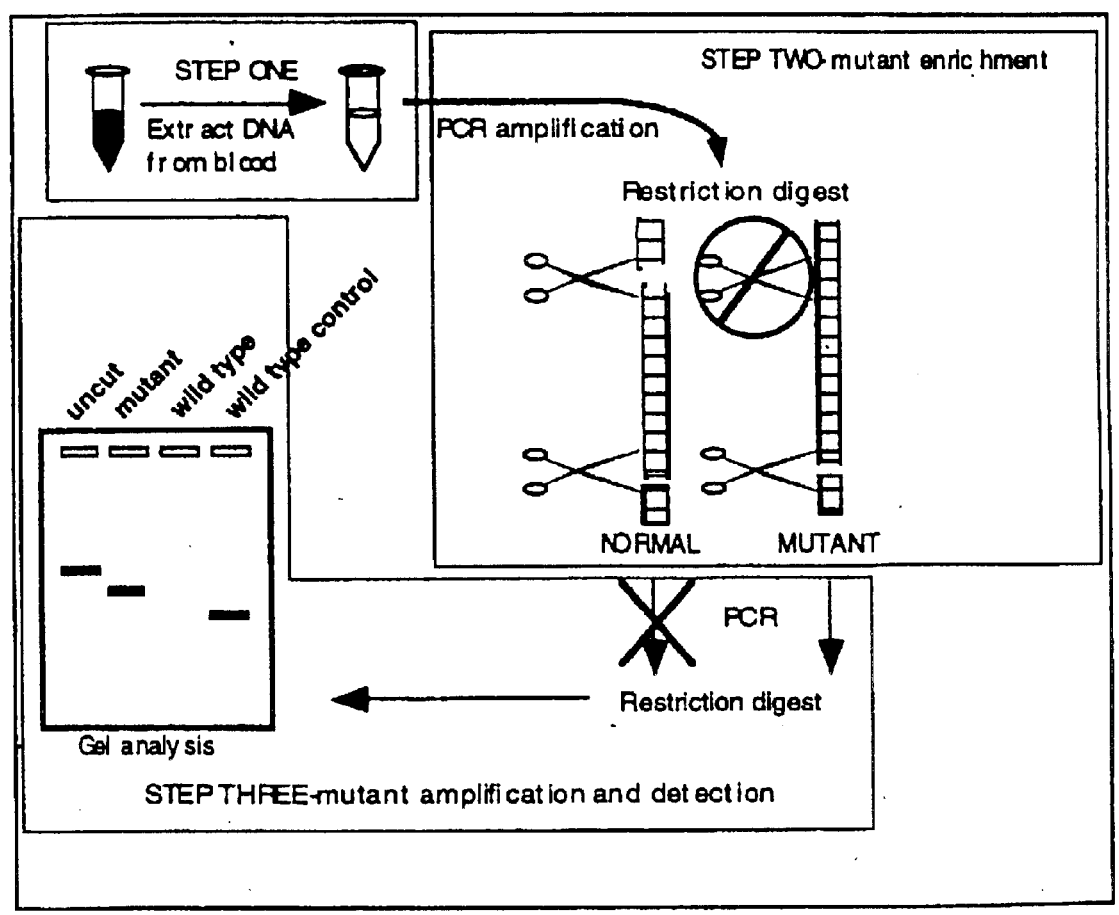
FIG. 2 is a schematic diagram of the serum oncogene detection assay of the invention.

All amplification assays included as a positive control DNA from a colon carcinoma cell line GEO known to contain a GGT→GCT mutation in codon 12 of the K-ras gene; a negative control containing wildtype K-ras sequences consisting of normal placenta tissue, and a negative control for PCR contamination consisting of water substituted for DNA in the reaction mixture. In addition, reactions were run in parallel without BstNI digestion to ensure amplification had occurred (as shown in FIG. 2). Routine precautions to prevent PCR contamination were employed in all amplification-based assays. The risk of contamination yielding falsely positive results was further minimized by repeating PCR assays on all patient plasma or serum samples 2–3 times on different days.

Figure 3:
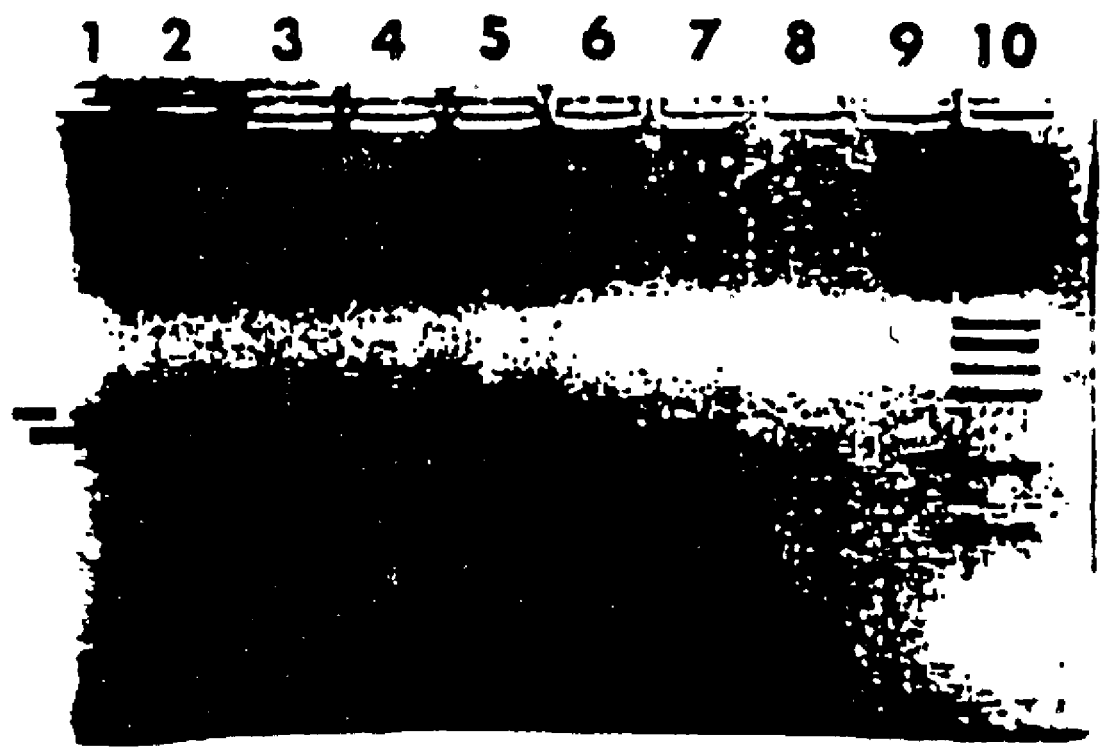
FIG. 3 illustrates detection of mutant ras oncogene DNA in serum of colorectal cancer patients. An assay of the invention was used to analyze serum from patients diagnosed with colorectal cancer, and DNA fragments corresponding to mutant K-ras oncogene detected by gel electrophoresis. In the PCR amplification products of extracellular serum DNA of each of patients A–D was found to a band at the position of mutated ras oncogene DNA (arrow). Uncut DNA is evident at a higher molecular weight only in the uncut control (dash) indicating complete digestion of all patient samples, while DNA fragments corresponding to wildtype ras oncogene DNA runs at a lower molecular weight and is evident in patient D and the negative control (arrowhead). The no-DNA control confirms absence of contamination. Lanes: 1, uncut control; 2, positive control (cell line with mutant ras oncogene); 3, 1:10,000 dilution of positive control; 4–7, patients A–D, respectively; 8, negative control (placenta with wild-type K-ras oncogene); 9, no-DNA control; 10, molecular weight markers (φX174 DNA cut with HaeIII).
Figure 4:
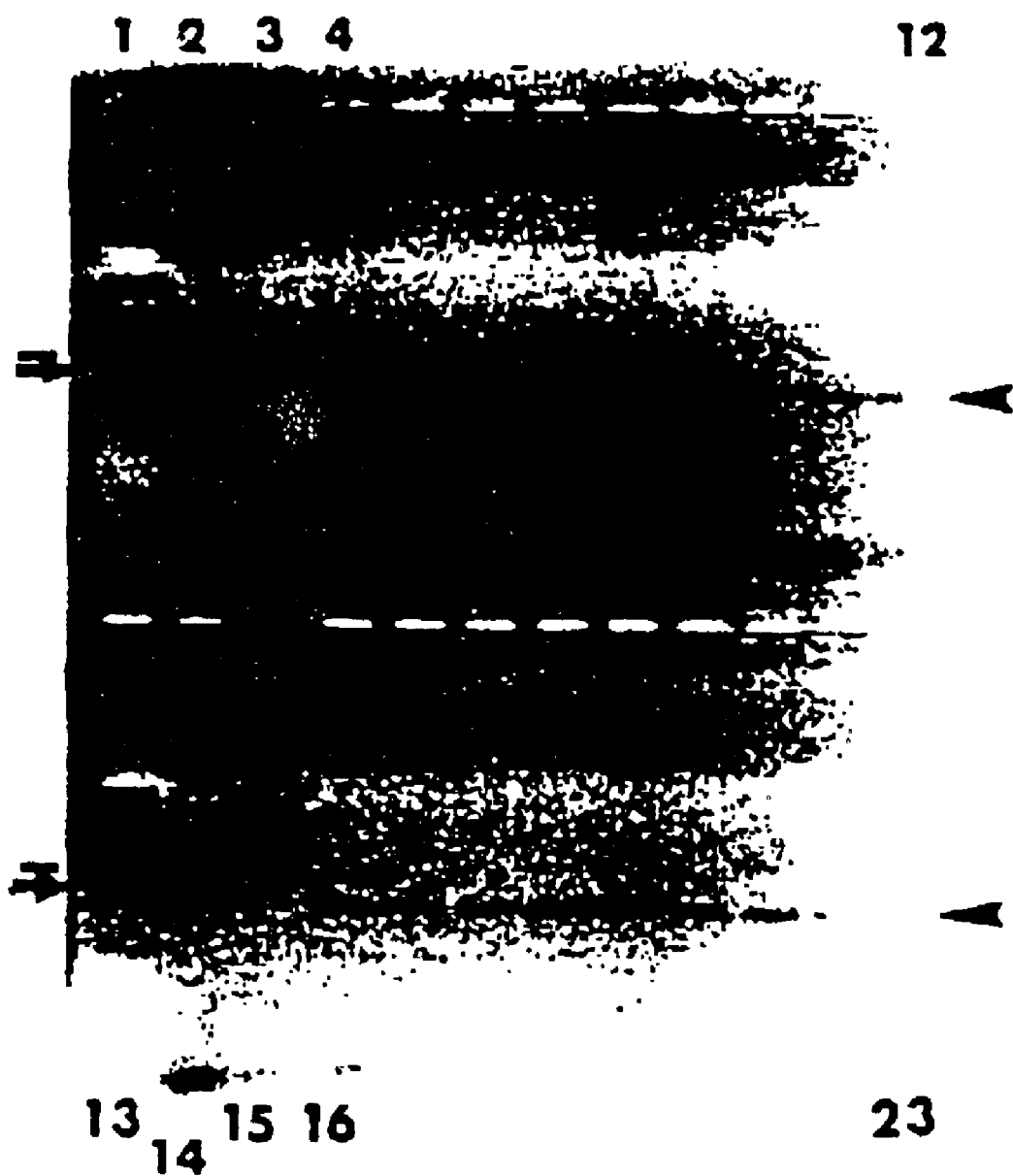
FIG. 4 shows the results of the assay described in Example 1. No mutant K-ras oncogene DNA was detected in serum of normal donors. The inventive assay as described in the Example was used to analyze serum from normal donors, and DNA fragments produced by PCR amplification were detected by gel electrophoresis. Each of the PCR products from normal donor DNAs showed only the lower molecular weight band indicating only wildtype K-ras oncogene DNA (arrowhead). The uncut control (dash) and mutated K-ras oncogene positive control (arrow) are as described in FIG. 3. Lanes: 1 and 13, molecular weight markers (φX174 DNA cut with HaeIII); 2 and 14, uncut control; 3, positive control (cell line with mutant K-ras oncogene); 15, 1:10,000 dilution of positive control; 4–12 and 16–23, normal donors.

Following gel electrophoresis, DNA fragments of the expected size were excised, reamplified, cloned into the pGEM-T vector (Promega), and the nucleotide sequence determined using a commercial sequencing kit (Sequenase 2.0, USB, Cleveland, Ohio). A minimum of two clones were sequenced for each PCR. Of the 6 patients with colorectal cancer, K-ras mutations were detected in the plasma or serum of 4 (67%) (shown in FIG. 3). The blood of all normal volunteers tested negative for K-ras mutations (shown in FIG. 4). In prototype experiments and using patient plasma or serum samples, this assay has been shown repeatedly to have a sensitivity capable of detecting 1 mutant K-ras molecule equivalent in a background of 100,000 to 1,000,000 wildtype K-ras molecules. However, to make certain that negative results were not due to failed amplifications, specimens were further tested by omitting the initial BstNI step digestion. In these experiments, a DNA fragment corresponding in size to the expected wildtype K-ras fragment was found in all cases (data not shown). In addition, the positive GEO control tested positive, and the negative placenta and water blank controls tested negative, in all PCR assays.

The above example describes detection of mutant K-ras in plasma or serum from patients with colorectal cancer, and the same methods are employed to detect K-ras mutations in plasma or serum from patients having any cancer associated with K-ras mutations, including colorectal, lung, pancreatic, and gastric cancers.

3. Premalignant Disease Detection Using CARD

In addition, the methods described herein can be used to detect premalignant or occult solid tumor disease. For example, a family history of colorectal cancer is a significant risk factor for the development of colorectal cancer, particularly if family history includes early onset.

Use of the CARD assay of the invention to detect extracellular oncogene-related DNA was performed on such a patient as follows. Plasma was collected from a 28 year old woman with recent rectal bleeding and a family history of colorectal cancer (one aunt who had died in early adulthood from colorectal cancer). The patient had undergone endoscopy and colonoscopy at the time of plasma collection, and had no clinical evidence of colorectal cancer. The patient's plasma was therefore subjected to CARD analysis for the detection of extracellular DNA related to the K-ras oncogene.

This assay was performed as follows:

Step one: Plasma DNA was co-precipitated with gelatin and recovered as described above.

Combined Steps two and three: A reaction mixture was prepared containing 35 μL of the extracted DNA solution, 50 mM KCl, 10 mM Tris-HCl (pH 9), 0.1% Triton X-100, 1.5 mM MgCl$_2$, 200 μM each dNTP, 15 pmol each of K-ras primers 1 and 2 (SEQ ID Nos.: 1 & 2), 4U BstNI restriction endonuclease (Stratagene, LaJolla, Calif.) and 1U Taq polymerase (Promega, Madison, Wis.). This reaction mixture was overlaid with mineral oil and thermocycled using a protocol wherein the reaction was incubated at 94° C. for 7 seconds, then at 60° C. for 3 min, then at 94° C. for 5 seconds, then at 60° C. for 3 min, and so on, so that at each cycle the denaturation time at 94° C. decreased by one second until the seventh cycle (having a denaturation time of 1 second), which was repeated for an additional 33 cycles, for a total of 40 cycles in the amplification reaction. After cycle 10, thermocycling was paused at 60° C. and an additional 10U of restriction enzyme added.

At the completion of the thermocycling reaction, 20 μL of the amplification/digestion mixture were removed into a fresh reaction tube and mixed with 10U BstNI in the appropriate buffer to a total volume of 30 μL and incubated at 60° C. for 60 min. A second 10U aliquot of BstNI was added and the reaction incubated for an additional 60 min at 60° C.

Figure 6:
FIG. 6 shows detection of mutant K-ras oncogene DNA in the plasma of a patient at high risk for development of CRC using the CARD assay. The assay was used to amplify extracellular DNA from a patient with a strong family history of CRC and no clinical signs or symptoms of disease on gross physical examination, as described in Example 1. The mutant K-ras oncogene is indicated (arrow). Lanes: 1, molecular weight markers (φX174 DNA cut with HaeIII); 2, uncut control; 3, positive control (cell line with mutant K-ras oncogene); 4, positive control, diluted 1:100,000; 5 and 6, negative plasma; 7, patient sample; 10, negative control (placental DNA), size of this fragment denoted by a dash to the left of the gel picture; 11, no-DNA negative control.

This digestion reaction product was analyzed by gel electrophoresis on a 3% agarose gel; the results of this analysis are shown in FIG. 6. All assays included a K-ras positive control comprising of DNA from a colon carcinoma cell line containing K-ras having a codon 12 mutation; a K-ras negative control consisting of normal placental tissue DNA; and a negative control for PCR contamination, comprising a water blank. Reactions were also performed in parallel without BstNI digestion as a control for PCR amplification. Routine precautions associated with amplification were employed in all amplification-based experiments.

The results of this assay, as shown in FIG. 6 demonstrated the presence of mutant K-ras extracellular DNA in the patient plasma sample (lane 7). These results demonstrate that the methods of the invention enables the detection of extracellular DNA related to mutated oncogenes associated with occult or premalignant solid tumor disease. The detection of extracellular DNA encoding a mutant K-ras oncogene known to be associated with colorectal cancer in a patient having no clinical signs or symptoms of colorectal neoplasia demonstrates that the instant assay increases diagnostic assay sensitivity and ability to detect premalignant or occult neoplasia early in the course of the disease. The ability of the methods of the invention to detect tumor-related DNA from premalignant or occult neoplastic disease patients provides the capacity to better direct prevention, early detection, intervention, monitoring and management of neoplasia and pre-neoplastic disease, and affords the opportunity for medical intervention earlier in the disease course than heretofore, increasing the likelihood of success of treatment and cure.

EXAMPLE 2

Detection of Extracellular bcl-2 DNA and bcl-2/IgH Translocations in Plasma or Serum 1. Background Follicular center cell lymphoma (follicular lymphoma) is the most common form of primary malignancy of the lymph nodes in the U.S., comprising more than half of all cases of lymphoma. Follicular lymphoma is generally a slowly progressive malignancy, with patient survival averaging several years to a decade or more. Standard treatment of follicular lymphoma depends on factors such as extent of disease and age, and typically involves multi-agent chemotherapy. Newer approaches to therapy include high dose chemotherapy with bone marrow transplantation and immunotherapy, either actively or passively induced. Because of the high rate of relapse among patients treated with standard regimens, and because of the general oncologic tenet that treating small amounts of tumor rather than large masses is more efficacious, there is a need for methods to detect minimal amounts of tumor in follicular lymphoma patients.

Follicular lymphomas are distinguished by a particular genetic alteration, the breaking and rejoining of chromosomes 14 and 18 to each other. This breaking, or translocation, results in the juxtaposition of two genes in a head-to-tail fashion: the oncogene bcl-2 on chromosome 18, which is known to play a role in the control of programmed cell death; and an immunoglobulin heavy chain gene (IgH) on chromosome 14. Uniting these two genes as a result of translocation causes a dysregulation of the bcl-2 gene. This is thought to be due to the fact that immunoglobulin heavy chain genes are typically activated in the lymphoid cells from which this malignancy derives, and in the translocation the adjacent bcl-2 gene inappropriately shares in the activation. Translocation occurs in approximately 80–90% of follicular lymphomas, and in two-thirds to three-quarters of these cases the translocation involves one of two well-characterized sites. The sites of frequent bcl-2 breakage fall within small areas (a few hundred base pairs) termed the Major Breakpoint-cluster Region (MBR) and the minor breakpoint-cluster region (mcr). The translocation at the immunoglobulin locus also occurs in restricted regions since the breakage mimics the normal immunoglobulin gene rearrangement process. The restricted nature of the translocation permits prediction in most cases of the DNA flanking the breakpoints, which thereby provides diagnostic nucleic acid fragments uniquely found in cells having this translocation.

2. Details of the Assay

The assay was performed in the following steps.

Step one: Four patients with follicular lymphoma had serum drawn prior to or early in a standard course of antineoplastic chemotherapy. Three of these patients had been previously demonstrated by PCR to have tumor cells containing a MBR translocation; the fourth patient had no PCR-detectable MBR or mcr translocation in tumor cells. Serum DNA was co-precipitated with gelatin and recovered as described above in Example 1.

Step two: Tumor specific bcl-2/IgH translocations were amplified using a non-radioactive PCR assay as follows. A reaction mixture was prepared containing 35 μL of the extracted DNA solution of Step One, 50 mM potassium chloride, 10 mM Tris buffer (pH 9.0), 0.1% Triton X-100, 1.5 mM magnesium chloride, 200 μM of each nucleotide triphosphate (dATP, dGTP, dCTP, and dTTP), 1 pmol oligonucleotide MBR comprising the sequence:
5'-TTAGAGAGTTGCTTTACGTG-3' (SEQ ID No.: 3), 1 pmol oligonucleotide $J_H$ (CON) comprising the sequence:
5'-ACCTGAGGAGACGGTGACC-3' (SEQ ID No.: 4), in a total volume of 48 μL. One Unit of Taq DNA polymerase (Fisher Chemical Co., Fairlawn, N.J.) diluted to 2 μL in the same buffer was added to each sample after samples had been pre-heated to 95° C.

The oligonucleotide MBR was constructed to contain the nucleotide sequence that is immediately upstream of the most frequent site of translocation in the bcl-2 gene (positions 4415–4434; Genbank Accession #I08038). The oligonucleotide $J_H$(CON) is constructed to contain consensus sequences to the 3' ends of the 6 $J_H$ segments of the immunoglobulin heavy chain gene, and will hybridize with each $J_H$ segment under the conditions of PCR amplification used herein. Thus, translocation of the bcl-2 gene into any of the $J_H$ regions permits specific and exponential amplification from the involved region using an upstream translocation primer such as MBR.

The reaction mixture was cycled 20 times using a thermocycling profile of 94° C. for 1 minute, 56.5° C. for 2 minutes, and 72° C. for 3 minutes in a Deltacycler thermocycler (Ericomp, San Diego, Calif.).

Step three: Two μL of the PCR mixture of Step Two was removed to a clean tube and a new reaction mixture was set up for the second round of amplification using the same components of the amplification reaction mixture as described above in Step Two, with the exception that 25 pmoles of oligonucleotide MBR-int having the sequence:
5'-GCCTGTTTCAACACAGACC-3' (SEQ ID No.: 5) (positions 4435-4453; Genbank Accession #I08038) and 25 pmoles of oligonucleotide $J_H$ (CON) (SEQ ID No.: 4) were used. The MBR-int primer lies internal to the MBR primer and increases the specificity of the second round of amplification. The same cycling conditions as above were employed for a total of 30 amplification cycles. The final amplification reaction products were analyzed by gel electrophoresis on a 3% agarose gel (NuSieve) in TBE buffer.

All amplification assays included a bcl-2/IgH positive control consisting of the lymphoma cell line MB-1 containing a diagnostic and well-characterized breakpoint (comprising the sequence at position 3110 of bcl-2: GTT..ctc..GG<u>AT</u>TGGACG translocated into the $J_H$ (6) immunoglobulin heavy chain gene, where N-nucleotide additions or N-insertions are in lower case and somatic mutations are underlined); a wildtype bcl-2/IgH negative control consisting of normal placenta tissue, and a PCR contamination negative control consisting of water substituted for DNA. Routine precautions to prevent PCR contamination were employed in all amplification-based work.

Figure 5:
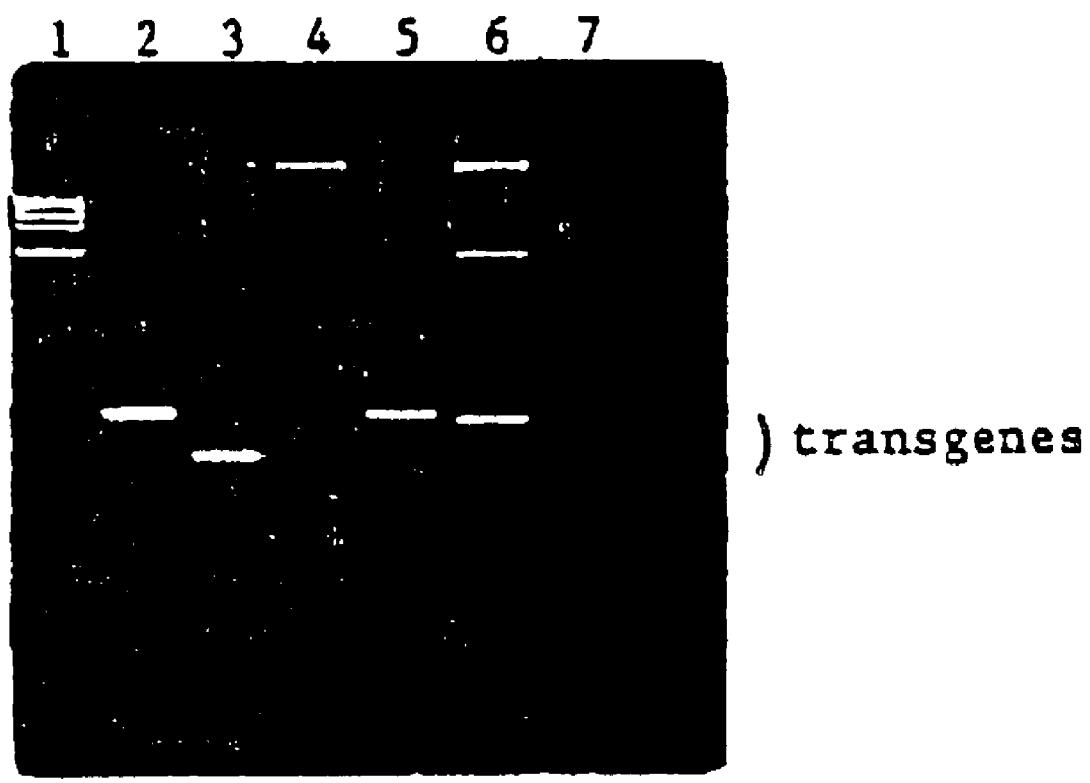
FIG. 5 shows the bcl-2/IgH transgene is detectable in the serum of follicular lymphoma patients. The assay was used to amplify extracellular DNA from 4 patients with follicular lymphoma, as described in Example 2. The transgene is identified in each patient known to have an amplifiable translocation (lanes 3, 5, 6), and not in the patient without such a translocation (lane 4). Lanes: 1, molecular weight markers (φX174 DNA cut with HaeIII); 2, positive control (cell line with bcl-2/IgH transgene); 3–6, patient serum; 7, no-DNA control.

Results from these assays are shown in FIG. 5. For the three patients with bcl-2/IgH translocations detectable in their tumor cells, identical DNA fragments corresponding to hemi-nested PCR amplification were detected in the extracellular DNA isolated from serum. The patient without a detectable translocation in tumor cell DNA (due to either lack of a translocation or a variant translocation not detectable with these primers) did not have a translocation-specific PCR product detectable in serum. All controls produced the expected fragments (or lack of fragments for the PCR negative controls).

A similar assay is used to detect bcl-2 sequences per se (i.e., without assaying for a specific translocation breakpoint within the bcl-2 gene). This is accomplished using a 3' PCR primer constructed to comprise the complement of a nucleotide sequence of bcl-2 at a defined distance 3' to the bcl-2 specific primer described above (SEQ ID No.: 3), substituted for the $J_H$(CON) primer described above (SEQ ID No.: 4) in PCR amplification reactions performed as described herein. This bcl-2 specific primer has the sequence 5'-GGAGGATCTTACCACGTGGA-3' (SEQ ID No.: 10). PCR amplification using this pair of bcl-2 specific amplification primers are useful for detecting extracellular DNA in patient serum or plasma independent of the specific translocation associated with lymphoma, and thus provides a method for detecting putative lymphoma-bearing patients not bearing well-characterized lymphoma-specific translocations, and for detecting bcl-2 related extracellular DNA associated with other (non-lymphoma) cancers.

EXAMPLE 3

Detection of Extracellular Mutant p53 DNA in Plasma or Serum

1. Background

The p53 oncogene is one of the most frequently mutated tumor suppressor genes in human cancer. Among other functions, it is a regulator of the cell cycle and is involved in programmed cell death, and its mutation permits unopposed cell proliferation. In colorectal cancer (described above in Example 1), approximately half of all CRCs contain mutations of the p53 oncogene (Greenblatt et al., 1994, *Cancer Res.* 54: 4855–78), and a survey of the EMBL Data Library of 360 published mutations of p53 in CRC cases indicates that 49% occur at 5 particular amino acids (Hollstein et al., 1994, *Nucleic Acids Res.* 22: 3551–5). Recent data indicate that p53 and K-ras mutations in CRC tend to be mutually exclusive, that is, tumors are commonly found with only one or the other, rarely both (Dix et al., 1995, *Diagn. Molec. Path.* 4: 261–265). These finding suggested that an assay for p53 gene mutations in extracellular DNA in serum or plasma would identify patients other than those identified using the K-ras assay described above in Example 1. The p53 mutational "hot spots" in colorectal cancer are amino acids 175, 245, 248, 273, and 282. This clustering of mutations may permit a panel or multiplex approach to the amplification-based assays disclosed herein using a number of primer pairs and restriction enzymes to identify affected patients (illustrated in Tables I–III below). Although CRC is exemplified in this Example, one of ordinary skill will appreciate that any other malignancy having p53 mutations can be analyzed using the assays of the invention.

2. Details of the Assay

The assay was performed using the following steps.

Step one: Extracellular DNA from patient plasma or serum is co-precipitated with gelatin as described above in Example 1.

Step two: Nucleic acid comprising mutant p53 oncogene sequences are amplified utilizing a non-radioactive PCR assay performed as follows. A reaction mixture is prepared as described above, containing 35 µL of the extracted extracellular DNA from plasma or serum, 50 mM potassium chloride, 10 mM Tris buffer (pH 9.0), 0.1% Triton X-100, 1.5 mM magnesium chloride, 200 µM apiece of each deoxynucleoside triphosphate (dATP, dGTP, dCTP, and dTTP), and the following pairs and amounts of the primers shown in Table I:

```
0.7 pmol exon 5 oligonucleotide 5'-primer 5'-GCAGTCACAGCACATGACG-3' and    (SEQ ID No.: 11)

0.5 pmol exon 5 oligonucleotide 3'-primer 5'-AATCAGAGGCCTGGGGAC-3' or;    (SEQ ID No.: 12)

0.7 pmol exon 7 oligonucleotide 5'-primer 5'-GGGCCTGTGTTATTCTCCTAGG-     (SEQ ID No.: 13)
                                            3' and 0.5 pmol exon 7 oligonucleotide 3'-primer 5'-CCAGTGTGATGATGGTGAGG-3' or;(SEQ ID No.: 14)

0.5 pmol exon 8 oligonucleotide 5'-primer 5'-GGACGGAACAGCTTTGAGGCG-      (SEQ ID No.: 15)
                                            3' and 0.5 pmol exon 8 oligonucleotide 3'-primer TCCCCGGGGCAGCGCGT;             (SEQ ID No.: 16)
``` and 1 Unit of Taq DNA polymerase (Fisher) in a final volume of 50 µL. One member of each primer pair is prepared having a sequence modification to create a non-naturally-occurring restriction enzyme site for the corresponding enzyme in Table I to serve as an internal control. Each of the activating mutations for each primer pair shown in Table I destroy a restriction enzyme site normally found in the p53 gene, thereby permitting enrichment of the samples for the mutant allele by restriction enzyme digestion prior to second round amplification (as described in Example 1). The amplification reaction mixture is thermocycled 15–20 times using a protocol of 94° C. for 48 seconds, 57° C. for 90 seconds (for exon 5 or 7 primers) or 61° C. for 90 seconds (for exon 8 primers), and 72° C. for 155 seconds in a Deltacycler thermocycler (Ericomp).

After amplification, 10 µL of the PCR mixture is removed to a clean tube and mixed with 1× reaction buffer and 10 units of the appropriate restriction enzyme for each primer pair shown in Table I, and incubated at the appropriate temperature for 90 min. A second aliquot of 10 units of restriction enzyme is added and the reaction continued for an additional 90 min.

Step three: Ten μL of the digested PCR mixture is transferred to a clean tube and a new amplification reaction mixture is prepared for a second round of amplification using the same constituents as in the first amplification, except that 35 pmoles of oligonucleotide 5'-primer (exons 5 and 7) or 25 pmoles of oligonucleotide 5'-primer (exons 8) and 25 pmoles of oligonucleotide 3'-primer (exons 5, 7 and 8) are used. The same thermocycling conditions are employed for 33–35 amplification cycles. A second restriction digestion is performed using 25 μL of the second step PCR product and 17 units of enzyme in a final volume of 35 μL. Digestions are performed for 60 min, followed by the addition of a second aliquot of 10 units of enzyme and a final digestion for an additional 60 min. The final digestion product was analyzed by gel electrophoresis on a 3% agarose gel (NuSieve) in TBE buffer. In the practice of this invention the production of elevated levels of non-specific DNA fragments produced by PCR may be anticipated. Hybridization with detectably-labeled specific probes may therefore be used to increase assay sensitivity.

The expected sizes of the wildtype, undigested PCR product DNA fragments are 130 bp (exon 5), 111 bp (exon 7) and 104 bp (exon 8). DNA fragments corresponding to wildtype alleles for exon 7 are cleaved to 7, 85, and 19 bp by MspI, and mutation at p53 positions 14069 or 14070 yields fragment sizes 7 and 104 bp. DNA fragments corresponding to wildtype alleles for exon 7 are cleaved to 82, 22, and 7 bp by AciI, and mutation at p53 positions 14060 or 14061 yields fragment sizes 104 and 7 bp. DNA fragments corresponding to wildtype alleles for exon 8 are cleaved to 19, 76, and 9 bp by BstNI, and mutation at p53 positions 14486 or 14487 yields fragment sizes 95 and 9 bp. DNA fragments corresponding to wildtype alleles for exon 8 are cleaved to 47, 52, and 5 bp by MspI, and mutation at p53 positions 14513 or 14514 yields fragment sizes 99 and 5 bp. The combination of specific amplification using the p53 primers described in Table I, digestion with the appropriate restriction enzymes and detection of DNA fragments of the expected sizes results in detection of extracellular DNA in plasma or serum corresponding to any of the expected mutant alleles of p53.

Alternatively, in a preferred embodiment, amplification can be performed using hemi-nested primers as shown in Table II that can provide more specific and rapid results in Step Three of the methods of the invention. In this assay, extracellular DNA is extracted as described above from patient plasma or serum. PCR amplification reactions are performed as described above, with the exception that 1 pmol of each of the appropriate external primers are used in the first PCR amplification reaction, these primers being described in Table II. The pattern of PCR primer utilization in these assays is summarized in Table III, wherein the first amplification is performed with the primer pairs labeled "Step Two" and the second amplification is performed with the primer pairs labeled "Step Three." For the first amplification reaction, the thermocycling protocols used is a total of 15 amplification cycles of 94° C. for one minute, 59° C. for two minutes, and 72° C. for two minutes in a thermocycler. All primer combinations described use this same cycling protocol. Upon completion of the first amplification reaction, 10 μL of the PCR mixture is removed to a clean tube and mixed with 1× reaction buffer and 10 Units of the appropriate restriction enzyme shown in Table I, and incubated at the appropriate temperature for 60 min. A second aliquot of 10 Units of restriction enzyme is added to each reaction and digestion continued for an additional 60 min.

The third step in the assay is an additional amplification reaction using the Step Three amplification primer pairs as shown in Table III. For these reactions, 10 μL of the digested PCR mixture is removed to a clean tube and a new amplification reaction mixture constructed as described above, substituting 25 pmoles of each of the Step Three primer pairs in Table III for the Step Two primer pairs used in the first amplification reaction. Thermocycling is performed for 33–35 amplification cycles under the same conditions as described above, with the exception that the annealing temperature for exon 5 and exon 7 primers is 58° C. and the annealing temperature for exon 8 primers is 60° C. After completion of the amplification reaction, a second restriction digestion is performed using 25 μL of the Step Three PCR product and 17 units of enzyme in a final volume of 35 μL. DNA fragments are digested for 60 min, followed by the addition of a second aliquot of 10 Units of enzyme and a final digestion for an additional 60 min. The final digestion product was analyzed by gel electrophoresis on a 3% agarose gel (NuSieve) in TBE buffer. The expected sizes of the DNA fragments obtained for the wildtype and mutant p53 alleles assayed using this method are those described above.

Detection of extracellular DNA in patient plasma or serum may be achieved using sera or plasma from patients having any cancer associated with p53 mutations, including cancers of the colon, rectum, bladder, breast, esophagus, liver, lung cervix, and brain, and sarcomas, lymphomas, leukemias, and melanomas. In particular, mutations in amino acid 249 are found more frequently in liver cancer and lung cancer than in any other primary site. This mutation also forms a large

TABLE I p53 mutation "hotspots" in CRC and assay reagents for detecting mutations

| Activating mutation(s) | amino acid | exon | 5' primer sequence | 3' primer sequence | Enzyme |
|---|---|---|---|---|---|
| 13103 | 175 | 5 | GCAGTCACAGCACATGACG | AATCAGAGGCCTGGGGAC | HhaI |
| 14060, 14061 | 245 | 7 | GGGCCTGTGTTATTCTCCTAGG | CCAGTGTGATGATGGTGAGG | Aci I |
| 14069, 14070 | 248 | 7 | GGGCCTGTGTTATTCTCCTAGG | CCAGTGTGATGATGGTGAGG | MspI |
| 14486, 14487 | 273 | 8 | GGACGGAACAGCTTTGAGGCG | TCCCCGGGGGCAGCGCGT | BstUI |
| 14513, 14514 | 282 | 8 | GGACGGAACAGCTTTGAGGCG | TCCCCGGGGGCAGCGCGT | MspI |

TABLE II p53 hemi-nested primers for amplifying mutation "hotspots" in CRC

| Mutation(s) | External primer | 5' primer sequence | 3' primer sequence |
|---|---|---|---|
| 13103 | GGGCCAGACCTAAGAGCAAT | GCAGTCACAGCACATGACG | AATCAGAGGCCTGGGGAC |
| 14060, 14061 | GCCTCCCCTGCTTGCCAC | GGGCCTGTGTTATTCTCCTAGG | CCAGTGTGATGATGGTGAGG |
| 14069, 14070 | GCCTCCCCTGCTTGCCAC | GGGCCTGTGTTATTCTCCTAGG | CCAGTGTGATGATGGTGAGG |
| 14486, 14487 | CTGATTTCCTTACTGCCTCTTGCCTT | GGACGGAACAGCTTTGAGGCG | TCCCCGGGGGCAGCGCGT |
| 14513, 14514 | CTGATTTCCTTACTGCCTCTTGCCTT | GGACGGAACAGCTTTGAGGCG | TCCCCGGGGGCAGCGCGT |

*Mutation numbering after Genbank Sequence X02469, Hsp53

TABLE III

Combinations of Nested Primer Pairs for p53 Amplification

| Activating mutation(s) | Primers used in Step Two | Primers used in Step Three |
|---|---|---|
| 13103 | External + 5' | 5' + 3' |
| 14060, 14061 | External + 3' | 5' + 3' |
| 14069, 14070 | External + 3' | 5' + 3' |
| 14486, 14487 | External + 3' | 5' + 3' |
| 14513, 14514 | External + 3' | 5' + 3' | proportion of all p53 mutations in those tumors (28% in liver, 6% in lung) (Hollstein et al., 1994, ibid.). This may be due to particular carcinogenic susceptibility of these organs. This fact may permit the use of a relatively specific assay to detect particular primary cancers in patients at risk, e.g., patients with cirrhosis who have an elevated risk of liver cancer, or smokers predisposed to lung cancer.

EXAMPLE 4

Prophetic Examples of the Use of the Assays of the Invention

The following examples are illustrative of clinical uses for the assays of the invention.

Case 1

A 26 year old asymptomatic man presents for evaluation after learning his 37 year old brother was recently diagnosed with colon cancer. Peripheral blood is drawn in order to evaluate the patients plasma for the presence of extracellular mutant K-ras DNA. Plasma extracellular DNA is extracted by the gelatin extraction method as described, followed by PCR amplification using K-ras primers with diagnostic restriction enzyme digestion sites as described. To increase the sensitivity of the assay, a two-step amplification assay is performed with digestion of PCR products in Step Two, followed by reamplification and final digestion in Step Three. The final digestion product is analyzed by gel electrophoresis on a 3% agarose gel for detection of mutant-specific DNA fragments. The presence of these DNA fragments in the patient's plasma indicates that mutant K-ras extracellular DNA is present in the patient's blood plasma. K-ras oncogene mutations are present in 40–50% of colon cancer, initially occurring in the premalignant adenoma stage, but persisting throughout transformation to frank malignancy and metastatic colon cancer. Although colon cancer is highly curable if diagnosed at an early stage, it is fatal when diagnosed at advanced metastatic stages. The positive results of the assay of the invention for this patient, in a setting of a strongly positive family history for colon cancer, are highly suggestive of either premalignant or malignant colon cancer. Such a patient would be advised to undergo colonoscopy, and if no lesion is found, to receive surveillance more frequently than would normally be given.

This hypothetical case illustrates how the invention can be used as a low-cost means for identifying patients at high-risk for cancer, specifically colon cancer, and to discriminate between such patients who should receive further, more aggressive and more expensive preventive care from those at lower risk who do not require such additional surveillance. The assay of the invention provides for the detection of either premalignant or malignant conditions prior to the metastatic state, and can thus play a role in clinical management of human cancer. Because K-ras mutations are also noted in other cancers, such as pancreatic and lung cancer, additional amplification reactions using a multiplex panel approach to detect multiple different tumor-associated extracellular DNAs, including for example p53, DCC, and APC DNA, permits a more exact discrimination of the potential tissue source of extracellular mutant oncogene DNA in plasma and serum, and informs clinical efforts for further diagnostic interventions including directing such efforts to those tissues most likely to comprise an occult neoplasm, while at the same time having the potential to eliminate the need for unnecessary screening of a variety of other tissues for neoplasia based on a failure to detect the appropriate collection of related extracellular DNAs.

Case 2

A 33 year old woman sees her local dermatologist after noting a "bleeding mole" on her back. Local excision diagnoses a malignant melanoma of 0.3 millimeter depth. Wide surgical re-excision is performed, and the patient is told she is likely cured and no further therapy is needed. Molecular analysis of the resected melanoma demonstrates that it is a mutant p53-positive tumor. Three months following her surgery the patient seeks a second opinion regarding the need for further therapy. Peripheral blood is drawn to evaluate the patient's plasma for the presence of extracellular mutant p53 oncogene DNA using the assays of the invention. Extracellular DNA is extracted from plasma as described above using the silica extraction method, followed by PCR amplification for extracellular mutant p53 DNA. p53-specific amplification products are detected by ELISA. In this case, the inventive assay detects the presence of mutant p53 in the patient's plasma matching the mutation found in the original tumor, with the presence of this DNA in plasma indicating latent malignant melanoma. Consequently, the patient is started on adjuvant therapy with interferon-alpha. Extracellular plasma p53 oncogene DNA levels are subsequently followed in a quantitative fashion using the assays methods of the invention. Blood is drawn from the patient every two months, and extracellular plasma DNA is extracted and analyzed by quantitative PCR amplification for mutant p53 DNA using biotinylated primers and an electrochemiluminescence-based detection means. Invention data demonstrate a rise in the patient's mutant p53-specific extracellular plasma DNA levels. As a consequence, interferon treatment is stopped, and the patient is enrolled into an experimental adjuvant therapy protocol.

This hypothetical case illustrates several uses of the invention, including the detection of latent cancer, prediction of disease prognosis and cancer recurrence following surgical excision, determination of the need for additional therapy, evaluation of the benefit of therapy and the need to change therapies, and further evaluation of the prognosis of patients as a result of therapy.

Case 3

A 76 year old man is found to have a pancreatic mass on CT scan imaging. His chest x-ray and colonoscopy are normal. The patient refuses to consider surgery because of the significant surgical risks. He elects to receive patient-specific therapy made possible by use of the invention. Since K-ras mutations are present in 80–90% of pancreatic cancers, peripheral blood is drawn to evaluate the plasma and characterize extracellular mutant K-ras DNA circulating in plasma using the assay methods of the invention. Extracellular DNA in plasma is extracted using the gelatin method as described, followed by PCR amplification and analysis of PCR products by agarose gel electrophoresis. Mutant K-ras amplification products are excised from the gel and the sequence of the K-ras specific fragment determined using a commercial kit. Detection of mutant K-ras sequences support the likelihood of the pancreatic mass being malignant. On the basis of the mutation sequence, a patient-specific therapy (i.e., specific to the patient's own cancer) is developed, in this case a ras vaccine specific to the mutant oncogene in this patient's pancreatic cancer.

In this hypothetical case, the invention is used not only to help confirm a suspected diagnosis of pancreatic cancer, but to develop a patient-specific therapy. Patient-specific therapies—i.e., therapies specifically designed for a given patient's cancer, or a given type of cancer—are possible when specific characteristics of the tumor are recognized. Since the invention results in amplification of pure tumor product, it becomes possible to characterize the tumor, in this case using sequence analysis. The assays methods of the invention thus permit an individual's tumor to be characterized without the need for biopsy or surgery. Thus it becomes possible to treat tumors even before they become clinically evident, by starting treatment at latent stages, pre-recurrence stages, or even pre-malignant stages. Early treatment of cancer before metastatic cells enter the bloodstream increases the likelihood of cure.

Case 4

A 36 year old woman who has three small children has been diagnosed with breast cancer two years ago. Her primary tumor had been shown to overexpress a mutated c-myc oncogene. She had been treated with surgery followed by a six month course of chemotherapy. In addition, her blood serum has been evaluated for extracellular c-myc oncogene DNA using the assay methods of the invention. Specifically, extracellular DNA in serum is extracted using the silica extraction method, followed by c-myc specific PCR amplification and ELISA detection of the c-myc specific PCR products. Although results for this patient are negative for some time, eventually her blood serum tests positive for extracellular c-myc oncogene DNA using the methods of the invention. These results suggest an impending cancer recurrence. A multiplex panel of amplification primer pairs is used to analyze the patient's extracellular DNA from serum, including primers specific for myc, ras, p53, EGFR, and HER-2/neu DNA, followed by sequencing. These data confirm that tumor characteristics are identical to those of the original primary breast cancer, confirming a recurrence of the patient's cancer rather than the development of a new primary tumor. Consequently, extracellular DNA in serum is measured quantitatively using a branched. DNA signal amplification assay, with measurements performed 2 months and 4 months later. Quantitative measurements indicate increasing levels of c-myc DNA, and allow extrapolation to predict that clinical recurrence will be noted in approximately 2 years. This information allows both the physician and the patient to plan future therapeutic options in the context of the patient's current social and family situation.

This hypothetical case illustrates the use of the invention to monitor patients following therapy for recurrence of their cancer, to determine characteristics of their tumor, and to predict prognosis. Breast cancer patients have a high incidence of second primaries, but the invention permits delineation of primary versus recurrent cancer by using a multiplex panel approach to evaluate tumor characteristics. Furthermore, since quantitative analysis permits clarification of prognosis, the patient is in a better position to plan therapy within the context of her social/family situation. Lastly, since the invention allows detection of tumor-derived extracellular DNA, and does not depend upon the presence of circulating cancer cells, recurrence can be detected at a very early stage (in this hypothetical case, 2 years before clinical detection), which increases the likelihood of effective therapy. Effective therapy can also be planned based upon tumor characteristics suggested by the extracellular DNA.

It should be understood that the foregoing disclosure emphasizes certain specific embodiments of the invention and that all modifications or alternatives equivalent thereto are within the spirit and scope of the invention as set forth in the appended claims.

We claim:

1. A method for detecting non-mutated tumor-associated DNA in blood plasma or serum from a human or animal with cancer, wherein said DNA is associated with cancer, the method comprising the steps of:
   a) extracting extracellular DNA from blood plasma or serum from a human or animal with cancer;
   b) amplifying or signal amplifying a portion of the extracted DNA qualitatively or quantitatively, wherein the portion comprises extracellular DNA associated with cancer;
   c) quantitatively or qualitatively detecting the amplified or signal amplified product.

2. The method of claim 1, wherein the amplified or signal amplified product is detected in subpart (c) using a detection method that is gel electrophoresis, immunological detection, nucleic acid hybridization using a fluorescent-, radioisotope-, antigenic- or chromogenically-labeled probe, Southern blot analysis, electrochemiluminescence, reverse dot blot hybridization, spectroscopy, or high performance liquid chromatography.

3. A method of identifying, diagnosing, monitoring, or evaluating cancer in a human or animal by detecting non-mutated DNA associated with cancer in blood plasma or serum from the human or animal, the method comprising the steps of:
   a) extracting extracellular DNA from a human's or an animal's blood plasma or serum;
   b) amplifying or signal amplifying a portion of the extracted DNA qualitatively or quantitatively, wherein the portion comprises non-mutated DNA associated with cancer;
   c) detecting the amplified or signal amplified product qualitatively or quantitatively; and
   d) identifying, diagnosing, monitoring, or evaluating cancer in said human or animal thereby.

4. A method for selecting a human for colonoscopy, the method comprising the steps of obtaining blood plasma or serum from the human and assaying the plasma or serum for the presence of extracellular, non-mutated tumor-associated DNA, wherein said DNA is associated with cancer, and selecting the human for colonoscopy when the presence of non-mutated tumor-associated DNA is detected.

5. A method for selecting a human for endoscopy, the method comprising the steps of obtaining blood plasma or serum from the human and assaying the plasma or serum for the presence of extracellular, non-mutated tumor-associated DNA, wherein said DNA is associated with cancer, and selecting the human for endoscopy when the presence of non-mutated tumor-associated DNA is detected.

6. A method for selecting a human for bronchoscopy, the method comprising the steps of obtaining blood plasma or serum from the human and assaying the plasma or serum for the presence of extracellular, non-mutated tumor-associated DNA, wherein said DNA is associated with cancer, and selecting the human for bronchoscopy when the presence of non-mutated tumor-associated DNA is detected.

7. A method for selecting a human for radiologic imaging, the method comprising the steps of obtaining blood plasma or serum from the human and assaying the plasma or serum for the presence of extracellular, non-mutated tumor-associated DNA, wherein said DNA is associated with cancer, and selecting the human for radiologic imaging when the presence of non-mutated tumor-associated DNA is detected.

8. A method for detecting non-mutated tumor-associated DNA in blood plasma or serum from a human or animal, wherein the non-mutated tumor-associated DNA is p16 DNA, bcl-2 DNA, Von Hippel-Lindau gene DNA, retinoblastoma gene DNA, her-2/neu DNA, epidermal growth factor DNA, or epidermal growth factor receptor DNA, the method comprising the steps of:

a) extracting DNA from blood plasma or serum from a human or animal;
   b) amplifying or signal amplifying a portion of the extracted DNA qualitatively or quantitatively, wherein the portion comprises non-mutated DNA that is p16 DNA, bcl-2 DNA, Von Hippel-Lindau gene DNA, retinoblastoma gene DNA, her-2/neu DNA, epidermal growth factor DNA, or epidermal growth factor receptor DNA;
   c) quantitatively or qualitatively detecting the amplified or signal amplified product.

9. A method of identifying, diagnosing, monitoring, or evaluating cancer in a human or animal by detecting non-mutated tumor-associated DNA in blood plasma or serum from the human or animal, wherein the non-mutated tumor-associated DNA is p16 DNA, bcl-2 DNA, Von Hippel-Lindau gene DNA, retinoblastoma gene DNA, her-2/neu DNA, epidermal growth factor DNA, or epidermal growth factor receptor DNA, the method comprising the step:

a) extracting DNA from blood plasma or serum from a human or animal;
   b) amplifying or signal amplifying a portion of the extracted DNA qualitatively or quantitatively, wherein the portion comprises non-mutated DNA that is p16 DNA, bcl-2 DNA, Von Hippel-Lindau gene DNA, retinoblastoma gene DNA, her-2/neu DNA, epidermal growth factor DNA, or epidermal growth factor receptor DNA;
   c) quantitatively or Qualitatively detecting the amplified or signal amplified product;
   d) identifying, diagnosing, monitoring, or evaluating cancer in said human or animal thereby.

10. A method for identifying, diagnosing, monitoring, or evaluating cancer in a human or animal, wherein one or more tumor-associated DNA species are detected in blood extracellular DNA from blood plasma or serum from the human or animal, wherein at least one of said DNA species is a non-mutated DNA associated with cancer, the method comprising the steps of:

a) extracting extracellular DNA from blood plasma or serum from a human or animal with cancer;
   b) amplifying or signal amplifying serially or in a multiplexed fashion a portion of the extracted DNA, wherein said portion of extracellular DNA comprises one or more tumor-associated DNA species, and wherein at least one DNA species is a non-mutated DNA associated with cancer;
   c) detecting the amplified or signal amplified product or products; and
   d) identifying, diagnosing, monitoring, or evaluating cancer in said human or animal thereby.

11. A method according to claim 10, wherein the serial or multiplexed amplification in step (b) is performed using a panel of primers for different DNA species.

12. A method according to claim 10, whereby the method is used to predict cancer recurrence following surgery or other cancer therapy.

13. A method according to claim 10, further comprising the step of selecting a cancer treatment for the human or animal.

* * * * *

UNITED STATES PATENT AND TRADEMARK OFFICE
CERTIFICATE OF CORRECTION

| | | |
|---|---|---|
| PATENT NO. | : 6,939,675 B2 | Page 1 of 1 |
| APPLICATION NO. | : 10/298816 | |
| DATED | : September 6, 2005 | |
| INVENTOR(S) | : Christopher D. Gocke et al. | |

It is certified that error appears in the above-identified patent and that said Letters Patent is hereby corrected as shown below:

In the Specification:

Please replace the priority claim starting

Column 1, line 6, "This application is a continuation U.S. Ser. No. 09/642,952, filed Aug. 21, 2000, now U.S. Pat. No. 6,521,409, which is a continuation of U.S. Ser. No. 08/818,058, filed Mar. 14, 1997, now U.S. Pat. No. 6,156,054, which is a continuation-in-part of U.S. Provisional Application, Ser. No. 60/028,180, filed Oct. 15, 1996, and U.S. Provisional Application Ser. No. 60/026,252, filed Sep. 17, 1996, and U.S. Provisional Application, Ser. No. 60/013,497, filed Mar. 15, 1996, each of which provisional applications is now abandoned, the entire disclosure of each of which is hereby incorporated by reference"

with

-- This application is a continuation of U.S. Patent Application Serial No. 09/642,952, filed August 21, 2000, now U.S. Patent No. 6,521,409, issued February 18, 2003, which is a continuation of U.S. Patent Application Serial No. 08/818,058, filed March 14, 1997, now U.S. Patent No. 6,156,504, issued December 5, 2000, which claims priority to U.S. Provisional Application Serial No. 60/028,180, filed October 15, 1996, U.S. Provisional Application No. 60/026,252, filed September 17, 1996, and U.S. Provisional Application No. 60/013,497, filed March 15, 1996, each of which provisional applications is now abandoned, the entire disclosure of each of which is hereby incorporated by reference --

Signed and Sealed this

Second Day of October, 2007

JON W. DUDAS
*Director of the United States Patent and Trademark Office*

SEQUENCE LISTING (1) GENERAL INFORMATION:

(iii) NUMBER OF SEQUENCES: 19

(2) INFORMATION FOR SEQ ID NO: 1:

(i) SEQUENCE CHARACTERISTICS:
    (A) LENGTH: 30 base pairs
    (B) TYPE: nucleic acid
    (C) STRANDEDNESS: single
    (D) TOPOLOGY: linear

```
     (ii) MOLECULE TYPE: cDNA (xi) SEQUENCE DESCRIPTION: SEQ ID NO: 1:

ACTGAATATA AACTTGTGGT AGTTGGACCT                                        30

(2) INFORMATION FOR SEQ ID NO: 2:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 2:

TCAAAGAATG TCCTGGACC                                                    19

(2) INFORMATION FOR SEQ ID NO: 3:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 3:

TTAGAGAGTT GCTTTACGTG                                                   20

(2) INFORMATION FOR SEQ ID NO: 4:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 4:

ACCTGAGGAG ACGGTGACC                                                    19

(2) INFORMATION FOR SEQ ID NO: 5:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 5:

GCCTGTTTCA ACACAGACC                                                    19

(2) INFORMATION FOR SEQ ID NO: 6:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 6:
```

ATTACTTGTG GTAGTTGGAG CTGH                                              24

(2) INFORMATION FOR SEQ ID NO: 7:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 7:

TGGCGTAGGC AAGAGTGC                                                     18

(2) INFORMATION FOR SEQ ID NO: 8:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 8:

GCACTCTTGC CTACGCCAD                                                    19

(2) INFORMATION FOR SEQ ID NO: 9:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 9:

CAAGCTCCAA CTACCACAAG TAAT                                              24

(2) INFORMATION FOR SEQ ID NO: 10:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 10:

GGAGGATCTT ACCACGTGGA                                                   20

(2) INFORMATION FOR SEQ ID NO: 11:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 11:

GCAGTCACAG CACATGACG                                                    19

(2) INFORMATION FOR SEQ ID NO: 12:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 12:

AATCAGAGGC CTGGGGAC                                                 18

(2) INFORMATION FOR SEQ ID NO: 13:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 13:

GGGCCTGTGT TATTCTCCTA                                               20

(2) INFORMATION FOR SEQ ID NO: 14:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 14:

CCAGTGTGAT GATGGTGAGG                                               20

(2) INFORMATION FOR SEQ ID NO: 15:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 15:

GGACGGAACA GCTTTGAGGC G                                             21

(2) INFORMATION FOR SEQ ID NO: 16:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 16:

TCCCCGGGGG CAGCGCGT                                                 18

(2) INFORMATION FOR SEQ ID NO: 17:

(i) SEQUENCE CHARACTERISTICS:
    (A) LENGTH: 20 base pairs

-continued

```
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 17:

GGGCCAGACC TAAGAGCAAT                                              20

(2) INFORMATION FOR SEQ ID NO: 18:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 18:

GCCTCCCCTG CTTGCCAC                                                18

(2) INFORMATION FOR SEQ ID NO: 19:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 19:

CTGATTTCCT TACTGCCTCT TGCTT                                        25
```